(12) United States Patent
Zhang et al.

(10) Patent No.: US 7,285,555 B2
(45) Date of Patent: Oct. 23, 2007

(54) 6-ARYL-7-HALO-IMIDAZO[1,2-A] PYRIMIDINES AS ANTICANCER AGENTS

(75) Inventors: Nan Zhang, Bayside, NY (US); Semiramis Ayral-Kaloustian, Tarrytown, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 456 days.

(21) Appl. No.: 10/950,542

(22) Filed: Sep. 24, 2004

(65) Prior Publication Data

US 2005/0065167 A1 Mar. 24, 2005

Related U.S. Application Data

(60) Provisional application No. 60/505,486, filed on Sep. 24, 2003.

(51) Int. Cl.
- A61K 31/519 (2006.01)
- C07D 487/04 (2006.01)
- A61P 35/04 (2006.01)

(52) U.S. Cl. .................................. 514/259.1; 544/281
(58) Field of Classification Search ................ 544/281; 514/259.1
See application file for complete search history.

(56) References Cited

U.S. PATENT DOCUMENTS

| | | | |
|---|---|---|---|
| 5,593,996 A | 1/1997 | Pees et al. | |
| 5,612,345 A | 3/1997 | Becher et al. | |
| 5,750,766 A | 5/1998 | Krummel et al. | |
| 5,756,509 A | 5/1998 | Pees | |
| 5,808,066 A | 9/1998 | Krummel et al. | |
| 5,817,663 A | 10/1998 | Pees et al. | |
| 5,854,252 A | 12/1998 | Pees et al. | |
| 5,948,783 A | 9/1999 | Pees et al. | |
| 5,955,252 A | 9/1999 | Goto et al. | |
| 5,965,561 A | 10/1999 | Pees et al. | |
| 5,981,534 A | 11/1999 | Pfrengle | |
| 5,985,883 A | 11/1999 | Pees | |
| 5,986,135 A | 11/1999 | Pfrengle et al. | |
| 5,994,360 A | 11/1999 | Pfrengle | |
| 6,020,338 A | 2/2000 | Pfrengle et al. | |
| 6,117,865 A | 9/2000 | Pees | |
| 6,117,876 A | 9/2000 | Pees et al. | |
| 6,124,301 A | 9/2000 | Aven et al. | |
| 6,156,925 A | 12/2000 | Meyer et al. | |
| 6,204,269 B1 | 3/2001 | Pfrengle et al. | |
| 6,242,451 B1 | 6/2001 | Pees | |
| 6,255,309 B1 | 7/2001 | Pees et al. | |
| 6,268,371 B1 | 7/2001 | Sieverding et al. | |
| 6,277,856 B1 | 8/2001 | Cotter et al. | |
| 6,284,762 B1 | 9/2001 | Pfrengle | |
| 6,297,251 B1 | 10/2001 | Pees et al. | |
| 6,387,848 B1 | 5/2002 | Aven et al. | |
| 2002/0045631 A1 | 4/2002 | Aven et al. | |
| 2002/0061882 A1 | 5/2002 | Pees et al. | |
| 2003/0055069 A1 | 3/2003 | Pees et al. | |

FOREIGN PATENT DOCUMENTS

| | | |
|---|---|---|
| EP | 0 550 113 A2 | 7/1993 |
| EP | 0 562 615 A1 | 9/1993 |
| EP | 0 770 615 B1 | 5/1997 |
| EP | 0 782 997 A2 | 7/1997 |
| EP | 0 550 113 B1 | 10/1997 |
| EP | 0 834 513 A2 | 4/1998 |
| EP | 0 562 615 B1 | 6/1998 |
| EP | 0 945 453 A1 | 9/1999 |
| EP | 0 989 130 A1 | 3/2000 |
| EP | 0 988 790 B1 | 5/2003 |
| EP | 0 943 241 B1 | 6/2003 |
| EP | 1 431 299 A1 | 6/2004 |
| FR | 2 784 381 | 4/2000 |
| JP | 2001/43978 A | 2/2001 |
| JP | 2001/43978 A1 | 2/2001 |
| WO | WO94/20501 A1 | 9/1994 |
| WO | WO98/41496 A1 | 9/1998 |
| WO | WO98/46607 A1 | 10/1998 |
| WO | WO98/46608 A1 | 10/1998 |
| WO | WO99/41255 A1 | 8/1999 |

(Continued)

OTHER PUBLICATIONS

M.C. Wani, et al.; J. Am. Chem. Soc.; vol. 93; pp. 2325-2327; 1971.
Ravindra Pratap Rao, et al.; J. Het.Chem.; pp. 1021-1023; 1973.
Ganapathi R. Revankar, et. al.; Journal of Medicinal Chemistry; vol. 18; No. 12; pp. 1253-1255; 1975.
Schiff, et al.; Nature; vol. 277; pp. 665-667; 1979.
Nirbhay Kumar; J. Biol. Chem.; vol. 256; No. 20; pp. 10435-10441; 1981.
E. Hamel, et al.; J. Biol. Chem.; vol. 259; No. 4; pp. 2501-2508; 1984.
Ding-Wu Shen, et al.; J. Biol. Chem., vol. 261, No. 17; pp. 7762-7770; 1986.
Tim McGrath and Melvin S. Center; Biochem. Biophys. Res. Commun.; vol. 145; No. 3; pp. 1171-1176; 1987.
William P. McGuire, et al.; Ann. Int. Med.; vol. III; pp. 273-279; 1989.

(Continued)

Primary Examiner—James O Wilson
Assistant Examiner—Susanna Moore
(74) Attorney, Agent, or Firm—Daniel B. Moran

(57) ABSTRACT

This invention relates to certain 6-aryl-7-halo-imidazo[1,2-a]pyrimidines or pharmaceutically acceptable salts thereof, and compositions containing said compounds or pharmaceutically acceptable salts thereof, wherein said compounds are anti-cancer agents useful for the treatment of cancer in mammals by promotion of microtubule polymerization. This invention further relates to a method of treating or inhibiting the growth of cancerous tumor cells and associated diseases in a mammal and further provides a method for the treatment or prevention of cancerous tumors that express multiple drug resistance (MDR) or are resistant because of MDR, in a mammal in need thereof which method comprises administering to said mammal an effective amount of said compounds or pharmaceutically acceptable salts thereof.

28 Claims, No Drawings

FOREIGN PATENT DOCUMENTS

| | | |
|---|---|---|
| WO | WO99/48893 A1 | 9/1999 |
| WO | WO 00/18227 A1 | 4/2000 |
| WO | WO 01/35738 A2 | 5/2001 |
| WO | WO 02/46195 A1 | 6/2002 |
| WO | WO 02/067679 A1 | 9/2002 |
| WO | WO 02/02563 A2 | 10/2002 |
| WO | WO 02/083676 A1 | 10/2002 |
| WO | WO 03/022850 A1 | 3/2003 |
| WO | WO 03/089433 A1 | 10/2003 |

OTHER PUBLICATIONS

Lori J. Goldstein, et al.; J. Natl. Cancer Inst. (Bethesda); vol. 81; pp. 116-124; 1989.

Eric K. Rowinsky, et al.; J. Natl. Cancer Inst.; vol. 82; No. 15; pp. 1247-1259; 1990.

Philip Skehan, et al.; J. Natl. Cancer Inst.; vol. 82; No. 13; pp. 1107-1112; 1990.

Frankie Ann Holmes, et al.; J. Natl. Cancer Inst.; vol. 83; No. 24; pp. 1797-1805, 1991.

Annette Bicher, et al.; Anti-Cancer Drugs; vol. 4; pp. 141-148; 1993.

Johannes J. Voegel, et al.; Helvetica Chimica Acta; vol. 76; pp. 2066-2069; 1993.

Elise C. Kohn, et al.; Journal of the National Cancer Institute; vol. 86; No. 1; pp. 18-24; 1994.

Robert A. Holton, et al.; J. Am. Chem. Soc.; vol. 116; No. 4; pp. 1597-1600; 1994.

Ernest Hamel; Med. Res. Rev.; vol. 16; pp. 207-231; 1996.

Sridhar K. Rabindran, et al.; Cancer Res.; vol. 58; pp. 5850-5858; 1998.

Carolyn M. Discafani, et al.; Biochemical Pharmacology; vol. 57; pp. 917-925; 1999.

Chun Li, et al.; Science & Medicine; vol. Jan./Feb.; pp. 38-47; 1999.

Eric K. Rowinsky and Anthony W. Tolcher; Cancer Principles and Practice; pp. 431-452; 2001.

Michael M. Gottesman; Annu. Rev. Med.; vol. 53; pp. 615-627; 2002.

Michael M. Gottesman, et al.; Nature Rev. Cancer; vol. 2; pp. 48-58; 2002.

Frank Loganzo, et al.; Cancer Res.; vol. 63; pp. 1838-1845; 2003.

P. Ribaud, European Journal of Cancer, vol. 33, Supp. 4, pp. S50-S54, 1997.

PCT International Search Report, Date of Mailing Jan. 27, 2005.

6-ARYL-7-HALO-IMIDAZO[1,2-A] PYRIMIDINES AS ANTICANCER AGENTS

"This application claims priority from now abandoned provisional Application No. 60/505,486 filed Sep. 24, 2003 the entire disclosure of which is hereby incorporated by reference"

FIELD OF THE INVENTION

The present invention relates to 6-aryl-7-halo-imidazo[1,2-a]pyrimidine compounds or pharmaceutically acceptable salts thereof, and compositions containing said compounds wherein said compounds are anti-cancer agents useful for the treatment of cancer in mammals. Compounds of the invention are useful for the treatment or prevention of cancerous tumors that express multiple drug resistance (MDR) or are resistant because of MDR. Further, compounds of the invention are useful for treating or inhibiting the growth of cancerous tumor cells and associated diseases in a mammal in need thereof by promotion of microtubule polymerization.

BACKGROUND OF THE INVENTION

Most of the cytostatics in use today either inhibit the formation of essential precursors for biosynthesis of DNA or block DNA polymerases or interfere with the template function of DNA because DNA was the primary target for developing therapeutic drugs for chemotherapy. Unfortunately, inhibition of the formation of essential precursors for biosynthesis of DNA or blocking DNA polymerases or interference with the template function of DNA also affects normal tissues.

Antimicrotubule drugs are a major category of anticancer agents (Rowinsky, E. K., and Tolcher, A. W. Antimicrotubule agents. In: V. T. Devita, Jr., S. Hellman, and S. A. Rosenberg (eds.), Cancer Principles and Practice, Ed. 6, pp. 431-452. Philadelphia: Lippincott Williams and Wilkins, 2001). They work by interfering with the function of cellular microtubules, particularly the mitotic spindle. The disruption of normal spindle function leads to apoptotic cell death.

Currently, there are three major classes of known antimicrotubule pharmacological agents. Each has a distinct binding region on β-tubulin and distinct effects on microtubule function. These classes are: 1) taxane-site agents which promote microtubule formation and stabilize microtubules; 2) vinca/peptide-site agents which destabilize microtubules and often induce formation of abnormal polymers or aggregates at high concentrations; and 3) colchicine-site agents which also destabilize microtubules and generally do not induce other polymers (Hamel, E. Antimitotic natural products and their interactions with tubulin. Med. Res. Rev., 16: 207-231,1996). Most of the ligands for all three classes of sites are natural products or semi-synthetic derivatives of natural products.

Paclitaxel and its semisynthetic derivative docetaxel (Taxotere®) interfere with microtubule formation and stabilize microtubules. Paclitaxel (Taxol®), is a diterpene isolated from the bark of the Western (Pacific) yew, *Taxus brevifolia* and is representative of a new class of therapeutic agent having a taxane ring system. It was additionally found in other members of the Taxacae family including the yew of Canada (*Taxus canadensis*) found in Gaspesia, eastern Canada and *Taxus baccata* found in Europe whose needles contain paclitaxel and analogs and hence provide a renewable source of paclitaxel and derivatives. The crude extract was tested for the first time during the 1960s and its active principle was isolated in 1971 and the chemical structure identified (M. C. Wani et al, J. Am. Chem. Soc., 93, 2325 (1971)). Further, a wide range of activity over melanoma cells, leukemia, various carcinomas, sarcomas and non-Hodgkin lymphomas as well as a number of solid tumors in animals was shown through additional testing. Paclitaxel and its analogs have been produced by partial synthesis from 10-deacetylbaccatin III, a precursor obtained from yew needles and twigs, and by total synthesis (Holton, et al., J. Am. Chem. Soc. 116:1597-1601 (1994) and Nicolaou, et al., Nature 367:630-634 (1994)). Paclitaxel has been demonstrated to possess antineoplastic activity. More recently, it was shown that the antitumor activity of paclitaxel is due to a promotion of microtubule polymerization (Kumar, N., J. Biol. Chem. 256:10435-10441 (1981); Rowinsky, et al., J. Natl. Cancer Inst., 82:1247-1259 (1990); and Schiff, et al., Nature, 277:665-667 (1979)). Paclitaxel has now demonstrated efficacy in several human tumors in clinical trials (McGuire, et al., Ann. Int. Med., 111:273-279 (1989); Holmes, et al., J. Natl. Cancer Inst., 83:1797-1805 (1991); Kohn et al., J. Natl. Cancer Inst., 86:18-24 (1994); and A. Bicker et al., Anti-Cancer Drugs, 4,141-148 (1993).

Two taxane-site agents (paclitaxel and docetaxel) and three vinca/peptide-site agents (vinblastine, vincristine, and vinorelbine) are used clinically to treat various human cancers. Taxanes have proven to be of greater utility against solid tumors (e.g., lung, breast, ovarian) than the vinca alkaloids, suggesting that agents that promote microtubule formation might be superior clinically to those that destabilize microtubules. Colchicine-site agents are not used therapeutically.

Despite the widespread clinical use of paclitaxel and docetaxel, these drugs have several limitations that create a need for improved agents. First, many tumors are inherently resistant (e.g., colon tumors) or become resistant after multiple cycles of treatment, at least in part due to the expression of drug transporters located in cancer cell membranes that pump the drugs out of cells and thereby decrease their efficacy (Gottesman, M. M. Mechanisms of cancer drug resistance. Annu. Rev. Med., 53: 615-627, 2002). The best known of these transporters is P-glycoprotein. Accordingly, there is a need for new agents with taxane-like effects on microtubule polymerization that are not substrates of P-glycoprotein or other such pumps and that therefore will overcome this cause of taxane resistance in patients.

Second, paclitaxel and docetaxel have poor water solubility and paclitaxel must be formulated in Cremophor EL, a vehicle that induces serious hypersensitivity reactions (Li, C. L., Newman, R. A., and Wallace, S. Reformulating paclitaxel. Science & Medicine, January/February: 38-47, 1999). Patients are typically premedicated with corticosteroids and antihistamines before administration of paclitaxel to minimize these toxicities. Accordingly, there is a need for new agents with taxane-like effects on microtubule polymerization that are highly water soluble and can be administered in physiological saline or other suitable non-toxic vehicle.

Third, paclitaxel is a natural product having a highly complex structure, and docetaxel is a closely related semi-synthetic derivative. Therefore there is a need for compounds which are readily available through synthesis, are structurally different from taxanes and which have taxane-like effects on microtubule polymerization.

Accordingly, there is still a need in the art for cytotoxic agents for use in cancer therapy. In particular, there is a need for cytotoxic agents which inhibit or treat the growth of tumors which have an effect similar to paclitaxel and interfere with the process of microtubule formation. Additionally, there is a need in the art for agents which accelerate tubulin polymerization and stabilize the assembled microtubules.

Further, it would be advantageous to provide new compounds which provide a method of treating or inhibiting cell proliferation, neoplastic growth and malignant tumor growth in mammals by administering compounds which have paclitaxel like anticancer activity.

Additionally, it would be advantageous to provide new compounds which provide a method for treating or inhibiting growth of cancerous tumors that express multiple drug resistance (MDR) or are resistant because of MDR.

Further, it would be advantageous to provide new compounds which provide a method of treating or inhibiting the growth of cancerous tumors in a mammal with inherent or acquired resistance to chemotherapeutic agents and in particular antimitotic agents.

Described in the art is the preparation and use of substituted triazolopyrimidines in agriculture as fungicides and are disclosed in U.S. Pat. Nos. 5,593,996; 5,756,509; 5,948,783; 5,981,534; 5,612,345; 5,994,360; 6,020,338; 5,985,883; 5,854,252; 5,808,066; 5,817,663; 5,955,252; 5,965,561; 5,986,135; 5,750,766; 6,117,865; 6,117,876; 6,124,301; 6,204,269; 6,255,309; 6,268,371; 6,277,856; 6,284,762; 6,297,251; 6,387,848; US Patent Application Publication US2002/0045631A1; US2002/0061882A1; US20030055069A1 and International Publication Numbers: WO98/46607; WO98/46608; WO99/48893; WO99/41255; WO00/18227; WO01/35738A2; WO02/46195A1; WO02/067679A1; WO02/083676A1; EPO 834513A2; EPO 782997A2; EPO550113B1; FR2784381A1; EPO 989130A1; WO98/41496; WO94/20501; EPO 945453A1; EPO 562615A1; EPO 562615B1; EP 0 550113A2; EP 0 943241B1; EP 0 988790 B1 and having the following general formula:

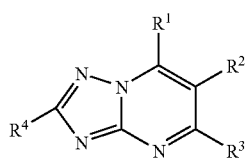

Also known are the use of triazolopyrimidines as anticancer agents having the structural formula

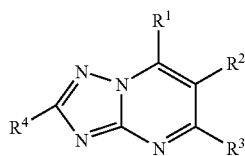

described in WO02/02563 A2.

5,7-Dihydroxyimidazo[1,2-a]pyrimidine without phenyl substitution at the 6-position is known (R. P. Rao et al, *J. Het. Chem.* 1021 (1973)). Also known is 5,7-dichloroimidazo[1,2-a]pyrimidine without phenyl substitution at the 6-position (G. R. Revankar, et al, *J. Med. Chem.* 18, 1253 (1975)).

EP 0,770,615 provides a process for the synthesis of dihaloazolopyrimidines of the formula

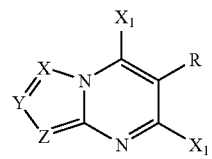

wherein:

$X_1$ is chlorine or bromine;

R is optionally substituted phenyl;

X, Y, and Z are $CR_1$ or N and further described is the synthesis of 5,7-dihydroxy-6-(2-chloro-6-fluorophenyl)benzimidazopyridine having the structural formula

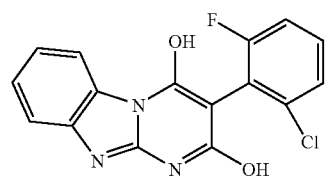

Described in JP2001043978 are diazaindolizines represented by the generic structure

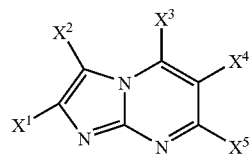

wherein said compounds are useful as electroluminescent elements.

Described in WO 03/022850 A1 are imidazo[1,2-a]pyrimidines represented by the following general formula

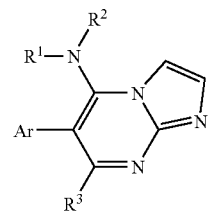

wherein said compounds are useful as fungicides.

The compounds of this invention are a new class of taxane-like agents that satisfy the hereinbefore described needs, and that differ in significant ways from the previously known classes of antimicrotubule compounds. The compounds of this invention bind at the vinca site of β-tubulin, yet they have many properties that are similar to taxanes and distinct from vinca-site agents. In particular, the compounds of this invention enhance the polymerization of microtubule-associated protein (MAP)-rich tubulin in the presence of GTP at low compound:tubulin molar ratios, in a manner similar to paclitaxel and docetaxel. Representative examples of the compounds of this invention also induce polymerization of highly purified tubulin in the absence of GTP under suitable experimental conditions, an activity that is a hallmark of taxanes. The compounds of this invention are potently cytotoxic for many human cancer cell lines in culture, including lines that overexpress the membrane transporters MDR (P-glycoprotein), MRP, and MXR, thus making them active against cell lines that are resistant to paclitaxel and vincristine.

SUMMARY OF THE INVENTION

In accordance with the present invention, there is provided compounds represented by Formula (I):

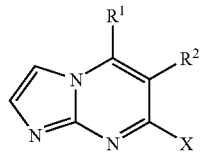

(I)

wherein:
$R^1$ is selected from

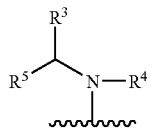

and $C_6$-$C_8$ cycloalkyl;
$R^2$ is a moiety of the formula

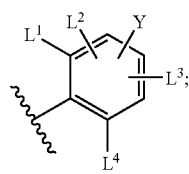

$R^3$ is H, or $C_1$-$C_3$ alkyl;
$R^4$ is H, or $C_1$-$C_3$ alkyl; or
$R^3$ and $R^4$ when optionally taken together form a 6 to 8 membered saturated heterocyclic ring having 1-2 nitrogen atoms, 0-1 oxygen atoms and 0-1 sulfur atoms, and optionally substituted with $C_1$-$C_3$ alkyl;
$R^5$ is H, $C_1$-$C_3$ alkyl or $C_1$-$C_3$ fluoroalkyl;
Y is a moiety of the formula —O(CH$_2$)$_n$Q;
n is an integer of 2, 3 or 4;
Q is —OH, or —NR$^6$R$^7$;
$R^6$ and $R^7$ are independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;

$L^1$, $L^2$, $L^3$, and $L^4$ are each independently H, F, Cl, Br or CF$_3$;
X is Cl or Br;

or pharmaceutically acceptable salts thereof.
A preferred embodiment of the invention are compounds according to Formula (Ia):

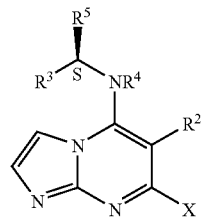

(Ia)

or pharmaceutically acceptable salts thereof.
A preferred embodiment of the invention are compounds according to Formula (Ib):

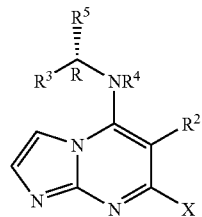

(Ib)

or pharmaceutically acceptable salts thereof.
A further preferred embodiment of the present invention provides compounds according to Formula (I) or pharmaceutically acceptable salts thereof wherein $R^2$ is a moiety of the formula

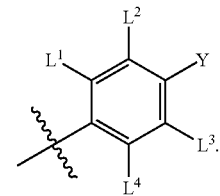

Among the more preferred group of compounds of this invention according to Formula (Ia) including pharmaceutically acceptable salts thereof are those wherein:
$R^2$ is

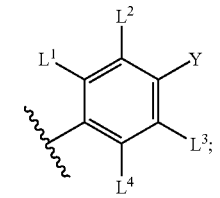

n is 3;
X is Cl or Br;
Y is a moiety of the formula —O—(CH$_2$)$_n$Q;

$R^3$ is H or methyl;
$R^4$ is H;
Q is $-NR^6R^7$;
$R^5$ is $CF_3$;
$R^6$ and $R^7$ are each independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are F;
$L^2$ and $L^3$ are H;

or pharmaceutically acceptable salts thereof.

Among the more preferred group of compounds of this invention according to Formula (Ib) including pharmaceutically acceptable salts thereof are those selected from the subgroups a) and b) below:
a)
$R^2$ is

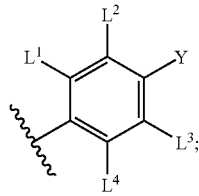

n is 3;
X is Cl or Br;
Y is a moiety of the formula $-O-(CH_2)_nQ$;
$R^3$ is H or methyl;
$R^4$ is H;
Q is $-NR^6R^7$;
$R^5$ is $CF_3$;
$R^6$ and $R^7$ are each independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are F;
$L^2$ and $L^3$ are H;

or pharmaceutically acceptable salts thereof and
b)
$R^2$ is

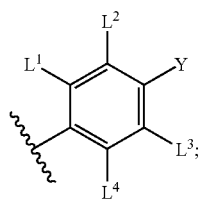

n is 3;
X is Cl;
Y is a moiety of the formula $-O(CH_2)_nQ$;
Q is $-NR^6R^7$;
$R^4$ is H;

$R^6$ is methyl;
$R^7$ is H or methyl;
$L^1$ and $L^4$ are F;
$L^2$ and $L^3$ are H;

or pharmaceutically acceptable salts thereof.

Preferred compounds of this invention according to Formula (I) including pharmaceutically acceptable salts thereof are those wherein $R^1$ is $C_6$-$C_8$ cycloalkyl.

Among the more preferred group of compounds of this invention according to Formula (I) including pharmaceutically acceptable salts thereof are the subgroup below:
$R^1$ is $C_6$-$C_8$ cycloalkyl;
$R^2$ is

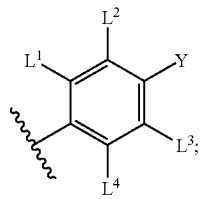

n is 3;
X is Cl;
Y is a moiety of the formula $-O(CH_2)_nQ$;
Q is $-NR^6R^7$;
$R^6$ is methyl;
$R^7$ is H or methyl;
$L^1$ and $L^4$ are F;
$L^2$ and $L^3$ are H;

or pharmaceutically acceptable salts thereof.

Among the most preferred group of compounds of this invention according to Formula (Ia) including pharmaceutically acceptable salts thereof are those of the group below:
$R^2$ is

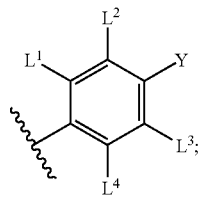

X is Cl;
n is 3;
Y is $-O(CH_2)_nQ$;
Q is $-NR^6R^7$;
$R^3$ is H or methyl;
$R^4$ is H;
$R^5$ is $CF_3$;
$R^6$ is methyl;
$R^7$ is H or methyl;
$L^1$ and $L^4$ are F;
$L^2$ and $L^3$ are H;

or pharmaceutically acceptable salts thereof.

Definitions

As utilized herein, the term "alkyl", alone or in combination, means a straight-chain or branched-chain alkyl radical containing from 1 to 3, preferably from 1 to 2, carbon atoms. Examples of such radicals include methyl, ethyl, n-propyl, isopropyl, and the like.

Fluoroalkyl means an alkyl group up to 3 carbon atoms wherein each hydrogen may be independently replaced by a fluorine atom.

The term alkali metal hydride includes lithium, potassium or sodium hydride.

The term alkali metal hydroxide includes lithium, potassium or sodium hydroxide.

The term alkali metal carbonate includes lithium, potassium or sodium carbonate.

Phenyl as used herein refers to a 6-membered carbon aromatic ring.

Cycloalkyl as used herein means a saturated carbocyclic monocyclic ring having from 6 to 8 carbon atoms optionally substituted with $C_1$-$C_3$ alkyl. Non-limiting representative examples include: cyclohexyl, cycloheptyl and cyclooctyl.

As used herein a saturated heterocyclic ring is a 4 to 6 membered ring with 1-2 nitrogen atoms, 0-1 oxygen atoms and 0-1 sulfur atoms optionally substituted with $C_1$-$C_3$ alkyl. Non-limiting representative examples include: morpholine, piperidine, pyrrolidine, piperazine, and azetidine.

The term t-BOC as used herein means tert-butoxy carbonyl.

Included in the scope of the present invention are (R) and (S) isomers of compounds of Formula (I) having a chiral center and the racemates thereof.

The present invention provides a method of treating or inhibiting the growth of cancerous tumor cells and associated diseases in a mammal by administering an effective amount of the compounds of Formula (I) and pharmaceutically acceptable salts thereof in need thereof.

The present invention also provides a method of treating or inhibiting the growth of cancerous tumor cells and associated diseases in mammals in need thereof by interacting with tubulin and microtubules by promotion of microtubule polymerization which comprises administering to said mammal an effective amount of the compounds of Formula (I) and pharmaceutically acceptable salts thereof.

The present invention further provides method for the treatment or prevention of tumors that express multiple drug resistance (MDR) or are resistant because of MDR in a mammal in need thereof which method comprises administering to said mammal an effective amount of such compounds or pharmaceutically acceptable salts thereof.

This invention also provides a method of promoting tubulin polymerization in a tubulin containing system by contacting said tubulin containing system with an effective amount of a compound of Formula (I) or pharmaceutically acceptable salts thereof.

Additionally this invention provides a method of stabilizing microtubules in a tubulin containing system which comprises contacting said tubulin containing system with an effective amount of a compound of Formula (I) or a pharmaceutically acceptable salt thereof.

Additionally this invention provides a method of treating, inhibiting the growth of, or eradicating a tumor in a mammal in need thereof wherein said tumor is resistant to at least one chemotherapeutic agent which comprises administering to said mammal an effective amount of the compounds of Formula (I) and pharmaceutically acceptable salts thereof.

Further this invention provides a compound of Formula (I) in combination or association with a pharmaceutically acceptable carrier. In particular, the present invention provides a pharmaceutical composition which comprises a compound of Formula (I) and a pharmaceutically acceptable carrier.

Additionally this invention provides a method of treating, inhibiting the growth of, or eradicating a tumor in a mammal in need thereof wherein said tumor is resistant to at least one chemotherapeutic agent which comprises administering to said mammal an effective amount of the compounds of Formula (I) and pharmaceutically acceptable salts thereof.

The compounds of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. Included in the scope of the present invention are (R) and (S) isomers of compounds of general Formula (I) having a chiral center and the racemates thereof. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

Optical isomers may be obtained in pure form by standard separation techiques or enantiomer specific synthesis.

Particularly preferred are isomers of Formula (I) wherein $R^1$ is the moiety

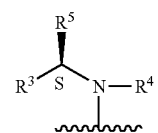

having the (S) configuration.

Specifically preferred compounds of this invention according to Formula (I) are the following compounds or pharmaceutically acceptable salts thereof selected from the group:

7-Chloro-6-{4-[3-(dimethylamino)propoxy]-2,6-difluorophenyl}-N-(2,2,2-trifluoroethyl)imidazo[1,2-a]pyrimidin-5-amine, 3-[4-(7-Chloro-5-cycloheptylimidazo[1,2-a]pyrimidin-6-yl)-3,5-difluorophenoxy]-N,N-dimethylpropan-1-amine, 7-Chloro-6-{4-[4-(dimethylamino)butoxy]-2,6-difluorophenyl}-N-(2,2,2-trifluoroethyl)imidazo[1,2-a]pyrimidin-5-amine, N-{3-[4-(7-chloro-5-cyclohexylimidazo[1,2-a]pyrimidin-6-yl)-3,5-difluorophenoxy]propyl}-N,N-dimethylamine, 7-chloro-6-{2,6-difluoro-4-[3-(methylamino)propoxy]phenyl}-N-(-2,2,2-trifluoro-1-methylethyl)imidazo[1,2-a]pyrimidin-5-amine and 7-chloro-6-{4-[3-(dimethylamino)propoxy]-2,6-difluorophenyl}-N-(-2,2,2-trifluoro-1-methylethyl)imidazo[1,2-a]pyrimidin-5-amine.

Specifically preferred compounds of this invention according to Formula (Ia) are the following compounds or pharmaceutically acceptable salts thereof selected from the group:

7-chloro-6-{2,6-difluoro-4-[3-(methylamino)propoxy]phenyl}-N-[(1S)-2,2,2-trifluoro-1-methylethyl]imidazo[1,2-a]pyrimidin-5-amine and 7-chloro-6-{4-[3-(dimethylamino)propoxy]-2,6-difluorophenyl}-N-[(1S)-2,2,2-trifluoro-1-methylethyl]imidazo[1,2-a]pyrimidin-5-amine.

Specifically preferred compounds of this invention according to Formula (Ib) are the following compounds or pharmaceutically acceptable salts thereof selected from the group:

7-chloro-6-{2,6-difluoro-4-[3-(methylamino)propoxy]phenyl}-N-[(1R)-2,2,2-trifluoro-1-methylethyl]imidazo[1,2-a]pyrimidin-5-amine and 7-chloro-6-{4-[3-(dimethylamino)propoxy]-2,6-difluorophenyl}-N-[(1R)-2,2,2-trifluoro-1-methylethyl]imidazo[1,2-a]pyrimidin-5-amine Also provided is a method of treating or inhibiting the growth of cancerous tumor cells and associated diseases in a mammal in need thereof which comprises administering an effective amount of a compound of Formula (II):

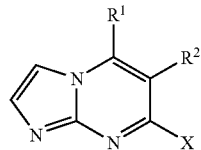

(II)

wherein:

$R^1$ is selected from

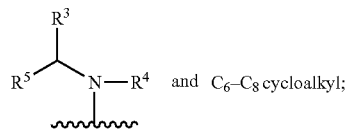

and $C_6$–$C_8$ cycloalkyl;

$R^2$ is a moiety of the formula

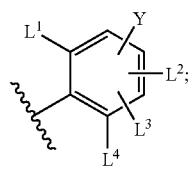

$R^3$ is H, or $C_1$-$C_3$ alkyl;
$R^4$ is H, or $C_1$-$C_3$ alkyl; or
$R^3$ and $R^4$ optionally taken together form a 6 to 8 membered saturated heterocyclic ring having 1-2 nitrogen atoms, 0-1 oxygen atoms and 0-1 sulfur atoms, and optionally substituted with $C_1$-$C_3$ alkyl;
$R^5$ is H, $C_1$-$C_3$ alkyl or $C_1$-$C_3$ fluoroalkyl;
Y is H, F, Cl, or a moiety of the formula —O(CH$_2$)$_n$Q;
n is an integer of 2, 3 or 4;
Q is —OH, or —NR$^6$R$^7$;
$R^6$ and $R^7$ are independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;

$L^1$, $L^2$, $L^3$, and $L^4$ each independently H, F, Cl, Br or CF$_3$;
X is Cl or Br;

or pharmaceutically acceptable salts thereof.

A preferred embodiment of the present invention provides a method of treating or inhibiting the growth of cancerous tumor cells and associated diseases in a mammal in need thereof which comprises administering an effective amount of a compound according to Formula (IIa):

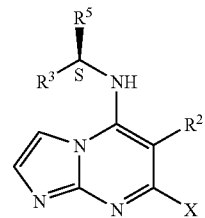

(IIa)

or pharmaceutically acceptable salts thereof.

A preferred embodiment of the present invention provides a method of treating or inhibiting the growth of cancerous tumor cells and associated diseases in a mammal in need thereof which comprises administering an effective amount of a compound according to Formula (IIb):

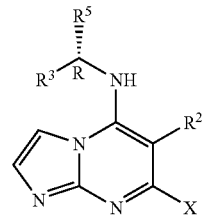

(IIb)

or pharmaceutically acceptable salts thereof.

An additionally preferred embodiment of the present invention provides a method of treating or inhibiting the growth of cancerous tumor cells and associated diseases in a mammal in need thereof which comprises administering an effective amount of a compound according to Formula (II) or pharmaceutically acceptable salts thereof wherein $R^1$ is $C_6$-$C_8$ cycloalkyl.

A further preferred embodiment of the present invention provides a method of treating or inhibiting the growth of cancerous tumor cells and associated diseases in a mammal in need thereof which comprises administering an effective amount of a compound according to Formula (II) or pharmaceutically acceptable salts thereof wherein $R^2$ is a moiety of the formula

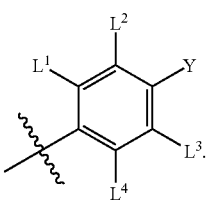

A more preferred embodiment of the present invention provides a method of treating or inhibiting the growth of cancerous tumor cells and associated diseases in a mammal in need thereof which comprises administering an effective amount of a compound according to Formula (II) including pharmaceutically acceptable salts thereof wherein:
$R^2$ is the moiety

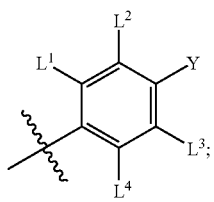

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method of treating or inhibiting the growth of cancerous tumor cells and associated diseases in a mammal in need thereof which comprises administering an effective amount of a compound according to Formula (IIa) including pharmaceutically acceptable salts thereof wherein:
$R^2$ is the moiety

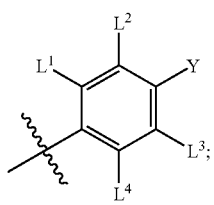

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method of treating or inhibiting the growth of cancerous tumor cells and associated diseases in a mammal in need thereof which comprises administering an effective amount of a compound according to Formula (II) including pharmaceutically acceptable salts thereof wherein:
$R^1$ is $C_6$-$C_8$ cycloalkyl;
$R^2$ is the moiety

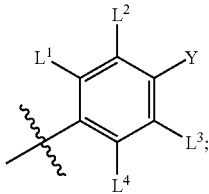

Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method of treating or inhibiting the growth of cancerous tumor cells and associated diseases in a mammal in need thereof which comprises administering an effective amount of a compound according to Formula (IIb) including pharmaceutically acceptable salts thereof wherein:
$R^2$ is the moiety

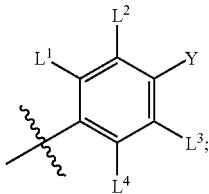

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A specific embodiment of the present invention provides a method of treating or inhibiting the growth of cancerous tumor cells and associated diseases in a mammal in need thereof which comprises administering an effective amount a compound or pharmaceutically acceptable salts thereof, selected from the group:
5-Azepan-1-yl-7-chloro-6-(2,4,6-trifluorophenyl)imidazo [1,2-a]pyrimidine,
7-Chloro-5-piperidin-1-yl-6-(2,4,6-trifluorophenyl)imidazo [1,2-a]pyrimidine,
7-Chloro-N-(2,2,2-trifluoroethyl)-6-(2,4,6-trifluorophenyl) imidazo[1,2-a]pyrimidin-5-amine,
7-Chloro-6-{4-[3-(dimethylamino)propoxy]-2,6-difluorophenyl}-N-(2,2,2-trifluoroethyl)imidazo[1,2-a]pyrimidin-5-amine,
7-Chloro-5-cycloheptyl-6-(2,4,6-trifluorophenyl)imidazo[1,2-a]pyrimidine,
3-[4-(7-Chloro-5-cycloheptylimidazo[1,2-a]pyrimidin-6-yl)-3,5-difluorophenoxy]-N,N-dimethylpropan-1-amine,
7-Chloro-6-{4-[4-(dimethylamino)butoxy]-2,6-difluorophenyl}-N-(2,2,2-trifluoroethyl)imidazo[1,2-a]pyrimidin-5-amine,
N-{3-[4-(7-chloro-5-cyclohexylimidazo[1,2-a]pyrimidin-6-yl)-3,5-difluorophenoxy]propyl}-N,N-dimethylamine,
7-chloro-6-{2,6-difluoro-4-[3-(methylamino)propoxy]phenyl}-N-(-2,2,2-trifluoro-1-methylethyl)imidazo[1,2-a]pyrimidin-5-amine and
7-chloro-6-{4-[3-(dimethylamino)propoxy]-2,6-difluorophenyl}-N-(-2,2,2-trifluoro-1-methylethyl)imidazo[1,2-a]pyrimidin-5-amine.

A specific embodiment of the present invention provides a method of treating or inhibiting the growth of cancerous tumor cells and associated diseases in a mammal in need thereof which comprises administering an effective amount of a compound or pharmaceutically acceptable salts thereof according to Formula (IIa) selected from the group:
7-chloro-6-{2,6-difluoro-4-[3-(methylamino)propoxy]phenyl}-N-[(1S)-2,2,2-trifluoro-1-methylethyl]imidazo[1,2-a]pyrimidin-5-amine and
7-chloro-6-{4-[3-(dimethylamino)propoxy]-2,6-difluorophenyl}-N-[(1S)-2,2,2-trifluoro-1-methylethyl]imidazo [1,2-a]pyrimidin-5-amine.

A specific embodiment of the present invention provides a method of treating or inhibiting the growth of cancerous tumor cells and associated diseases in a mammal in need thereof which comprises administering an effective amount of a compound or pharmaceutically acceptable salts thereof according to Formula (IIb) selected from the group:
7-chloro-6-{2,6-difluoro-4-[3-(methylamino)propoxy]phenyl}-N-[(1R)-2,2,2-trifluoro-1-methylethyl]imidazo[1,2-a]pyrimidin-5-amine and
7-chloro-6-{4-[3-(dimethylamino)propoxy]-2,6-difluorophenyl}-N-[(1R)-2,2,2-trifluoro-1-methylethyl]imidazo[1,2-a]pyrimidin-5-amine.

Further provided is a method of promoting tubulin polymerization in a tubulin containing system by contacting said tubulin containing system with an effective amount of a compound of formula (II) or pharmaceutically acceptable salts thereof wherein:

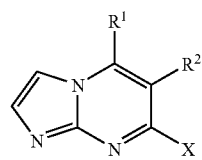
(II)

wherein:
$R^1$ is selected from

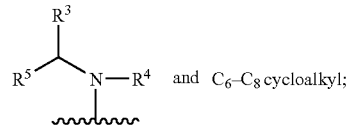

$R^2$ is a moiety of the formula

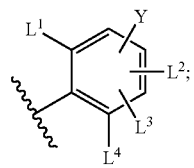

$R^3$ is H, or $C_1$-$C_3$ alkyl;
$R^4$ is H, or $C_1$-$C_3$ alkyl; or
$R^3$ and $R^4$ optionally taken together form a 6 to 8 membered saturated heterocyclic ring having 1-2 nitrogen atoms, 0-1 oxygen atoms and 0-1 sulfur atoms, and optionally substituted with $C_1$-$C_3$ alkyl;
$R^5$ is H, $C_1$-$C_3$ alkyl or $C_1$-$C_3$ fluoroalkyl;
Y is H, F, Cl, or a moiety of the formula —O($CH_2$)$_n$Q;
n is an integer of 2, 3 or 4;
Q is —OH, or —NR$^6$R$^7$;
$R^6$ and $R^7$ are independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$, $L^2$, $L^3$, and $L^4$ each independently H, F, Cl, Br or $CF_3$;
X is Cl or Br;
or pharmaceutically acceptable salts thereof.

A preferred embodiment of the present invention provides a method of promoting tubulin polymerization in a tubulin containing system by contacting said tubulin containing system with an effective amount of a compound of Formula (IIa):

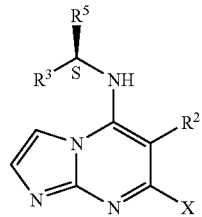
(IIa)

or pharmaceutically acceptable salts thereof.

A preferred embodiment of the present invention provides a method of promoting tubulin polymerization in a tubulin containing system by contacting said tubulin containing system with an effective amount of a compound of Formula (IIb):

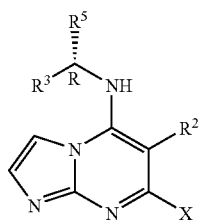

(IIb)

or pharmaceutically acceptable salts thereof.

An additionally preferred embodiment of the present invention provides a method of promoting tubulin polymerization in a tubulin containing system by contacting said tubulin containing system with an effective amount of a compound of Formula (II) or pharmaceutically acceptable salts thereof wherein $R^1$ is $C_6$-$C_8$ cycloalkyl.

This invention provides a method of promoting tubulin polymerization in a tubulin containing system by contacting said tubulin containing system with an effective amount of a compound of formula (II) wherein $R^2$ is a moiety of the formula

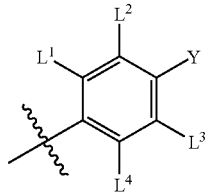

or pharmaceutically acceptable salts thereof.

A more preferred embodiment of the present invention provides a method of promoting tubulin polymerization in a tubulin containing system with an effective amount of a compound of Formula (IIa) including pharmaceutically acceptable salts thereof wherein:
$R^2$ is the moiety

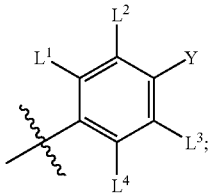

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method of promoting tubulin polymerization in a tubulin containing system by contacting said tubulin containing system with an effective amount of a compound of Formula (II) including pharmaceutically acceptable salts thereof are those wherein:
$R^1$ is $C_6$-$C_8$ cycloalkyl;
$R^2$ is the moiety

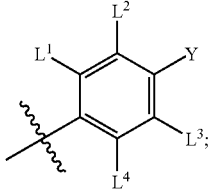

Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$alkyl;
$L^1$ and $L^4$ are each F;
$L^2$ and $L^3$ are each H;
X is Cl;

or pharmaceutically acceptable salts thereof.

A more preferred embodiment of the present invention provides a method of promoting tubulin polymerization in a tubulin containing system by contacting said tubulin containing system with an effective amount of a compound of Formula (IIb) including pharmaceutically acceptable salts thereof wherein:
$R^2$ is the moiety

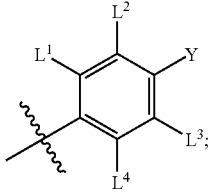

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;
Q is —NR$^6$R$^7$; $R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$alkyl;
$L^1$ and $L^4$ are each F;
$L^2$ and $L^3$ are each H;
X is Cl;

or pharmaceutically acceptable salts thereof.

A specific embodiment of the present invention provides a method of promoting tubulin in a tubulin containing system by contacting said tubulin containing system with an effective amount of a compound or pharmaceutically acceptable salts thereof according to Formula (II) selected from the group:

5-Azepan-1-yl-7-chloro-6-(2,4,6-trifluorophenyl)imidazo[1,2-a]pyrimidine,
7-Chloro-5-piperidin-1-yl-6-(2,4,6-trifluorophenyl)imidazo[1,2-a]pyrimidine,
7-Chloro-N-(2,2,2-trifluoroethyl)-6-(2,4,6-trifluorophenyl)imidazo[1,2-a]pyrimidin-5-amine,
7-Chloro-6-{4-[3-(dimethylamino)propoxy]-2,6-difluorophenyl}-N-(2,2,2-trifluoroethyl)imidazo[1,2-a]pyrimidin-5-amine,
7-Chloro-5-cycloheptyl-6-(2,4,6-trifluorophenyl)imidazo[1,2-a]pyrimidine,
3-[4-(7-Chloro-5-cycloheptylimidazo[1,2-a]pyrimidin-6-yl)-3,5-difluorophenoxy]-N,N-dimethylpropan-1-amine,
7-Chloro-6-{4-[4-(dimethylamino)butoxy]-2,6-difluorophenyl}-N-(2,2,2-trifluoroethyl)imidazo[1,2-a]pyrimidin-5-amine,
N-{3-[4-(7-chloro-5-cyclohexylimidazo[1,2-a]pyrimidin-6-yl)-3,5-difluorophenoxy]propyl}-N,N-dimethylamine,
7-chloro-6-{2,6-difluoro-4-[3-(methylamino)propoxy]phenyl}-N-(-2,2,2-trifluoro-1-methylethyl)imidazo[1,2-a]pyrimidin-5-amine and
7-chloro-6-{4-[3-(dimethylamino)propoxy]-2,6-difluorophenyl}-N-(-2,2,2-trifluoro-1-methylethyl)imidazo[1,2-a]pyrimidin-5-amine.

A specific embodiment of the present invention provides a method of promoting tubulin polymerization in a tubulin containing system by contacting said tubulin containing system with an effective amount of a compound or pharmaceutically acceptable salts thereof according to Formula (IIa) selected from the group:

7-chloro-6-{2,6-difluoro-4-[3-(methylamino)propoxy]phenyl}-N-[(1S)-2,2,2-trifluoro-1-methylethyl]imidazo[1,2-a]pyrimidin-5-amine and
7-chloro-6-{4-[3-(dimethylamino)propoxy]-2,6-difluorophenyl}-N-[(1S)-2,2,2-trifluoro-1-methylethyl]imidazo[1,2-a]pyrimidin-5-amine.

A specific embodiment of the present invention provides a method of promoting tubulin polymerization in a tubulin containing system by contacting said tubulin containing system with an effective amount of a compound or pharmaceutically acceptable salts thereof according to Formula (IIb) selected from the group:

7-chloro-6-{2,6-difluoro-4-[3-(methylamino)propoxy]phenyl}-N-[(1R)-2,2,2-trifluoro-1-methylethyl]imidazo[1,2-a]pyrimidin-5-amine and
7-chloro-6-{4-[3-(dimethylamino)propoxy]-2,6-difluorophenyl}-N-[(1R)-2,2,2-trifluoro-1-methylethyl]imidazo[1,2-a]pyrimidin-5-amine.

The present invention further provides a method of stabilizing microtubules in a tubulin containing system which comprises contacting said tubulin containing system with an effective amount of a compound of Formula (II):

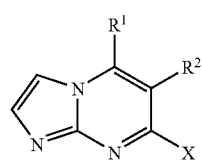

(II)

wherein:
$R^1$ is selected from

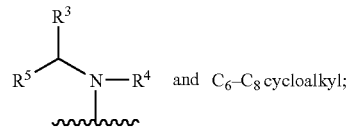

$R^2$ is a moiety of the formula

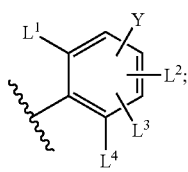

$R^3$ is H, or $C_1$-$C_3$ alkyl;
$R^4$ is H, or $C_1$-$C_3$ alkyl; or
$R^3$ and $R^4$ optionally taken together form a 6 to 8 membered saturated heterocyclic ring having 1-2 nitrogen atoms, 0-1 oxygen atoms and 0-1 sulfur atoms, and optionally substituted with $C_1$-$C_3$ alkyl;
$R^5$ is H, $C_1$-$C_3$ alkyl or $C_1$-$C_3$ fluoroalkyl;
Y is H, F, Cl, or a moiety of the formula —O(CH$_2$)$_n$Q;
n is an integer of 2, 3 or 4;
Q is —OH, or —NR$^6$R$^7$;
$R^6$ and $R^7$ are independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$, $L^2$, $L^3$, and $L^4$ each independently H, F, Cl, Br or CF$_3$;
X is Cl or Br;
or pharmaceutically acceptable salts thereof.

A preferred embodiment of the present invention provides a method of stabilizing microtubules in a tubulin containing system which comprises contacting said tubulin containing system with an effective amount of a compound of Formula (IIa):

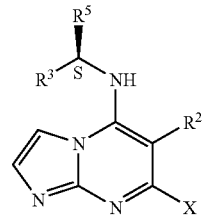

(IIa)

or pharmaceutically acceptable salts thereof.

A preferred embodiment of the present invention provides a method of stabilizing microtubules in a tubulin containing system which comprises contacting said tubulin containing system with an effective amount of a compound of Formula (IIb):

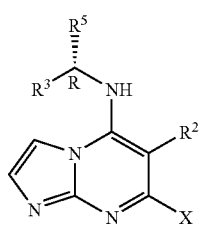

(IIb)

or pharmaceutically acceptable salts thereof.

An additionally preferred embodiment of the present invention provides a method of stabilizing microtubules in a mammal in need thereof by administering an effective amount of compounds of Formula (II) or pharmaceutically acceptable salts thereof wherein $R^1$ is $C_6$-$C_8$ cycloalkyl.

A further preferred embodiment of the present invention provides a method of stabilizing microtubules in a tubulin containing system which comprises contacting said tubulin containing system with an effective amount of a compound of Formula (II) or pharmaceutically acceptable salts thereof wherein $R^2$ is a moiety of the formula

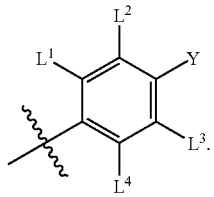

A more preferred embodiment of the present invention provides a method of stabilizing microtubules in a tubulin containing system which comprises contacting said tubulin containing system with an effective amount of a compound of Formula (IIa) including pharmaceutically acceptable salts thereof wherein:
$R^2$ is the moiety

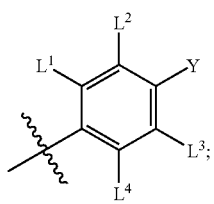

$R^3$ is H, or $C_1$-$C_3$ alkyl;
$R^4$ is H;
$R^5$ is $C_1$-$C_3$ fluoroalkyl;
Y is F, or a moiety —$O(CH_2)_nQ$;
n is 3;
Q is —$NR^6R^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method of stabilizing microtubules in a tubulin containing system which comprises contacting said tubulin containing system with an effective amount of a compound of Formula (II) including pharmaceutically acceptable salts thereof wherein:
$R^1$ is $C_6$-$C_8$ cycloalkyl;
$R^2$ is the moiety

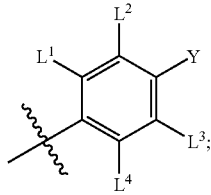

Y is F, or a moiety —$O(CH_2)_nQ$;
n is 3;
Q is —$NR^6R^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method of stabilizing microtubules in a tubulin containing system which comprises contacting said tubulin containing system with an effective amount of a compound of Formula (IIb) including pharmaceutically acceptable salts thereof wherein:
$R^2$ is the moiety

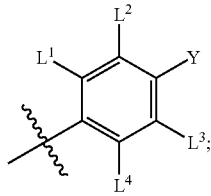

$R^3$ is H, or $C_1$-$C_3$ alkyl;
$R^4$ is H;
$R^5$ is $C_1$-$C_3$ fluoroalkyl;
Y is F, or a moiety —$O(CH_2)_nQ$;
n is 3;
Q is —$NR^6R^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_0$-$C_3$ alkyl;
$L^1$ and $L^4$ are each F;
$L^2$ and $L^3$ are each H;
X is Cl;

or pharmaceutically acceptable salts thereof.

A specific embodiment of the present invention provides a method of stabilizing microtubules in a tubulin containing system which comprises contacting said tubulin containing system with an effective amount of a compound of Formula (II) or pharmaceutically acceptable salts thereof according to Formula (II) selected from the group:
5-Azepan-1-yl-7-chloro-6-(2,4,6-trifluorophenyl)imidazo[1,2-a]pyrimidine,
7-Chloro-5-piperidin-1-yl-6-(2,4,6-trifluorophenyl)imidazo[1,2-a]pyrimidine,
7-Chloro-N-(2,2,2-trifluoroethyl)-6-(2,4,6-trifluorophenyl)imidazo[1,2-a]pyrimidin-5-amine,
7-Chloro-6-{4-[3-(dimethylamino)propoxy]-2,6-difluorophenyl}-N-(2,2,2-trifluoroethyl)imidazo[1,2-a]pyrimidin-5-amine,
7-Chloro-5-cycloheptyl-6-(2,4,6-trifluorophenyl)imidazo[1,2-a]pyrimidine,
3-[4-(7-Chloro-5-cycloheptylimidazo[1,2-a]pyrimidin-6-yl)-3,5-difluorophenoxy]-N,N-dimethylpropan-1-amine,
7-Chloro-6-{4-[4-(dimethylamino)butoxy]-2,6-difluorophenyl}-N-(2,2,2-trifluoroethyl)imidazo[1,2-a]pyrimidin-5-amine,
N-{3-[4-(7-chloro-5-cyclohexylimidazo[1,2-a]pyrimidin-6-yl)-3,5-difluorophenoxy]propyl}-N,N-dimethylamine,
7-chloro-6-{2,6-difluoro-4-[3-(methylamino)propoxy]phenyl}-N-(-2,2,2-trifluoro-1-methylethyl)imidazo[1,2-a]pyrimidin-5-amine and
7-chloro-6-{4-[3-(dimethylamino)propoxy]-2,6-difluorophenyl}-N-(-2,2,2-trifluoro-1-methylethyl)imidazo[1,2-a]pyrimidin-5-amine.

A specific embodiment of the present invention provides a method of stabilizing microtubules in a tubulin containing system which comprises contacting said tubulin containing system with an effective amount of a compound of Formula (IIa) or pharmaceutically acceptable salts thereof selected from the group:
7-chloro-6-{2,6-difluoro-4-[3-(methylamino)propoxy]phenyl}-N-[(1S)-2,2,2-trifluoro-1-methylethyl]imidazo[1,2-a]pyrimidin-5-amine and
7-chloro-6-{4-[3-(dimethylamino)propoxy]-2,6-difluorophenyl}-N-[(1S)-2,2,2-trifluoro-1-methylethyl]imidazo[1,2-a]pyrimidin-5-amine.

A specific embodiment of the present invention provides a method of stabilizing microtubules in a tubulin containing system which comprises contacting said tubulin containing system with an effective amount of a compound of Formula (IIb) or pharmaceutically acceptable salts thereof according to Formula (IIb) selected from the group:
7-chloro-6-{2,6-difluoro-4-[3-(methylamino)propoxy]phenyl}-N-[(1R)-2,2,2-trifluoro-1-methylethyl]imidazo[1,2-a]pyrimidin-5-amine and
7-chloro-6-{4-[3-(dimethylamino)propoxy]-2,6-difluorophenyl}-N-[(1R)-2,2,2-trifluoro-1-methylethyl]imidazo[1,2-a]pyrimidin-5-amine.

Also provided is a method for the treatment or prevention of tumors that express multiple drug resistance (MDR) or are resistant because of MDR in a mammal in need thereof which method comprises administering to said mammal an effective amount of a compound of formula (II):

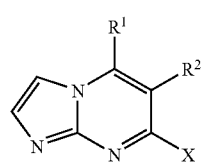

(II)

wherein:
$R^1$ is selected from

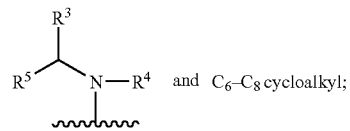

$R^2$ is a moiety of the formula

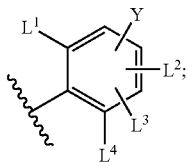

$R^3$ is H, or $C_1$-$C_3$ alkyl;
$R^4$ is H, or $C_1$-$C_3$ alkyl; or
$R^3$ and $R^4$ when optionally taken together form a 6 to 8 membered saturated heterocyclic ring having 1-2 nitrogen atoms, 0-1 oxygen atoms and 0-1 sulfur atoms, and optionally substituted with $C_1$-$C_3$ alkyl;
$R^5$ is H, $C_1$-$C_3$ alkyl or $C_1$-$C_3$ fluoroalkyl;
Y is H, F, Cl, or a moiety of the formula —O(CH$_2$)$_n$Q;
n is an integer of 2, 3 or 4;
Q is —OH, or —NR$^6$R$^7$;
$R^6$ and $R^7$ are independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$, $L^2$, $L^3$, and $L^4$ each independently H, F, Cl, Br or CF$_3$;
X is Cl or Br;

or pharmaceutically acceptable salts thereof.

A preferred embodiment of the present invention provides a method for the treatment or prevention of tumors that express multiple drug resistance (MDR) or are resistant because of MDR in a mammal in need thereof which method comprises administering an effective amount of a compound of Formula (IIa):

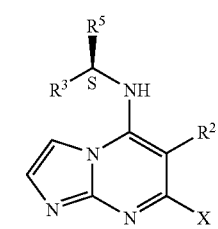

(IIa)

or pharmaceutically acceptable salts thereof.

A preferred embodiment of the present invention provides a method for the treatment or prevention of tumors that express multiple drug resistance (MDR) or are resistant because of MDR in a mammal in need thereof which method comprises administering an effective amount of a compound of Formula (IIb):

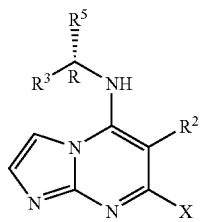

or pharmaceutically acceptable salts thereof.

An additionally preferred embodiment of the present invention provides a method for the treatment or prevention of tumors that express multiple drug resistance (MDR) or are resistant because of MDR in a mammal in need thereof which method comprises administering an effective amount of a compound of Formula (II) or pharmaceutically acceptable salts thereof wherein $R^1$ is $C_6$-$C_8$ cycloalkyl.

A further preferred embodiment of the present invention provides a method for the treatment or prevention of tumors that express multiple drug resistance (MDR) or are resistant because of MDR in a mammal in need thereof which method comprises administering an effective amount of a compound of Formula (II) or pharmaceutically acceptable salts thereof wherein $R^2$ is a moiety of the formula

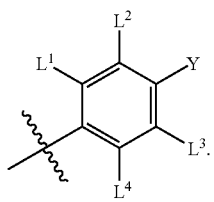

A more preferred embodiment of the present invention provides a method for the treatment or prevention of tumors that express multiple drug resistance (MDR) or are resistant because of MDR in a mammal in need thereof which method comprises administering an effective amount of a compound of Formula (IIa) including pharmaceutically acceptable salts thereof wherein:
$R^2$ is the moiety

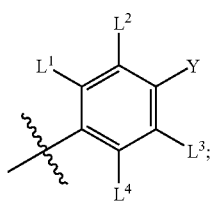

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method for the treatment or prevention of tumors that express multiple drug resistance (MDR) or are resistant because of MDR in a mammal in need thereof which method comprises administering an effective amount of a compound of Formula (II) including pharmaceutically acceptable salts thereof wherein:
$R^1$ is $C_6$-$C_8$ cycloalkyl;
$R^2$ is the moiety

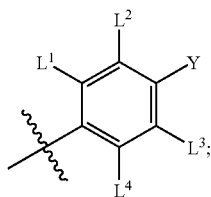

Y is F, or a moiety —O(CH$_2$)$_n$Q;
n is 3;
Q is —NR$^6$R$^7$;
$R^6$ and $R^7$ are each independently H or a $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are each F;
$L^2$ and $L^3$ are each H;
X is Cl;

or pharmaceutically acceptable salts thereof.

A more preferred embodiment of the present invention provides a method for the treatment or prevention of tumors that express multiple drug resistance (MDR) or are resistant because of MDR in a mammal in need thereof which comprises administering an effective amount of compounds according to Formula (IIb) including pharmaceutically acceptable salts thereof wherein:
$R^2$ is the moiety

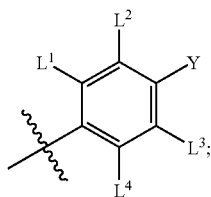

$R^3$ is H, or $C_1$-$C_3$ alkyl;
$R^4$ is H;
$R^5$ is $C_1$-$C_3$ fluoroalkyl;
Y is F, or a moiety —O(CH$_2$)$_n$Q;
n is 3;

Q is —NR⁶R⁷; R⁶ and R⁷ are each independently H or a C₁-C₃ alkyl; or

R⁶ and R⁷ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with R⁸;

R⁸ is C₁-C₃alkyl;
L¹ and L⁴ are each F;
L² and L³ are each H;
X is Cl;

or pharmaceutically acceptable salts thereof.

A specific embodiment of the present invention provides a method for the treatment or prevention of tumors that express multiple drug resistance (MDR) or are resistant because of MDR in a mammal in need thereof by administering an effective amount of a compound or pharmaceutically acceptable salts thereof according to Formula (II) selected from the group:

5-Azepan-1-yl-7-chloro-6-(2,4,6-trifluorophenyl)imidazo [1,2-a]pyrimidine,

7-Chloro-5-piperidin-1-yl-6-(2,4,6-trifluorophenyl)imidazo [1,2-a]pyrimidine,

7-Chloro-N-(2,2,2-trifluoroethyl)-6-(2,4,6-trifluorophenyl) imidazo[1,2-a]pyrimidin-5-amine, 7-Chloro-6-{4-[3-(dimethylamino)propoxy]-2,6-difluorophenyl}-N-(2,2,2-trifluoroethyl)imidazo[1,2-a]pyrimidin-5-amine, 7-Chloro-5-cycloheptyl-6-(2,4,6-trifluorophenyl)imidazo[1,2-a]pyrimidine, 3-[4-(7-Chloro-5-cycloheptylimidazo[1,2-a]pyrimidin-6-yl)-3,5-difluorophenoxy]-N,N-dimethylpropan-1-amine, 7-Chloro-6-{4-[4-(dimethylamino)butoxy]-2,6-difluorophenyl}-N-(2,2,2-trifluoroethyl)imidazo[1,2-a]pyrimidin-5-amine, N-{3-[4-(7-chloro-5-cyclohexylimidazo[1,2-a]pyrimidin-6-yl)-3,5-difluorophenoxy]propyl}-N,N-dimethylamine, 7-chloro-6-{2,6-difluoro-4-[3-(methylamino)propoxy]phenyl-N-(-2,2,2-trifluoro-1-methylethyl)imidazo[1,2-a]pyrimidin-5-amine and 7-chloro-6-{4-[3-(dimethylamino)propoxy]-2,6-difluorophenyl}-N-(-2,2,2-trifluoro-1-methylethyl)imidazo[1,2-a]pyrimidin-5-amine.

A specific embodiment of the present invention provides a method for the treatment or prevention of tumors that express multiple drug resistance (MDR) or are resistant because of MDR in a mammal in need thereof by administering an effective amount of a compound or pharmaceutically acceptable salts thereof according to Formula (IIa) selected from the group:

7-chloro-6-{2,6-difluoro-4-[3-(methylamino)propoxy]phenyl}-N-[(1S)-2,2,2-trifluoro-1-methylethyl]imidazo[1,2-a]pyrimidin-5-amine and 7-chloro-6-(4-[3-(dimethylamino)propoxy]-2,6-difluorophenyl}-N-[(1S)-2,2,2-trifluoro-1-methylethyl]imidazo [1,2-a]pyrimidin-5-amine.

A specific embodiment of the present invention provides a method for the treatment or prevention of tumors that express multiple drug resistance (MDR) or are resistant because of MDR in a mammal in need thereof by administering an effective amount of a compound or pharmaceutically acceptable salts thereof according to Formula (IIb) selected from the group:

7-chloro-6-{2,6-difluoro-4-[3-(methylamino)propoxy]phenyl}-N-[(1R)-2,2,2-trifluoro-1-methylethyl]imidazo[1,2-a]pyrimidin-5-amine and 7-chloro-6-{4-[3-(dimethylamino)propoxy]-2,6-difluorophenyl}-N-[(1R)-2,2,2-trifluoro-1-methylethyl]imidazo[1,2-a]pyrimidin-5-amine.

Additionally this invention provides a method of treating, inhibiting the growth of, or eradicating a tumor in a mammal in need thereof wherein said tumor is resistant to at least one chemotherapeutic agent which comprises administering to said mammal an effective amount of the compounds of formula (II) and pharmaceutically acceptable salts thereof.

DETAILED DESCRIPTION OF THE INVENTION

The compounds of this invention may be prepared from: (a) commercially available starting materials (b) known starting materials which may be prepared as described in literature procedures or (c) new intermediates described in the schemes and experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps. Appropriate consideration must be made as to the protection of reactive functional groups to prevent undesired side reactions.

Substituents on the starting materials may be incompatible with some of the reaction conditions. Such restrictions to the substituents which are compatible with the reaction conditions will be apparent to one skilled in the art. Reactions were run under inert atmospheres where appropriate.

Compounds of Formulae (I) and (II) where R¹ is

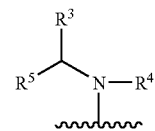

can be prepared by a process shown in Scheme I, in which R², R³, R⁴, R⁵, and X are as hereinbefore defined. Reacting compound (III, U.S. Pat. No. 6,156,925) with 2-aminoimidazole (IV) under alkaline conditions, using tertiary amines, such as tributylamine, at a temperature up to 190° C., provides compound (V). Halogenation with halogenating agents, POX₃ where X is Cl or Br such as phosphorous oxychloride or phosphorous oxybromide gives 5,7-dihalo compound (VI). Replacement of the 5-chloro or 5-bromo of 5,7-dihalo compound (VI) with an excess of an amine (VII) in a suitable solvent, such as dimethylsulfoxide or dimethylformamide provides compound of the formula (II) where R¹ is

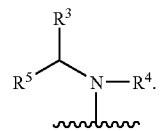

Scheme I:

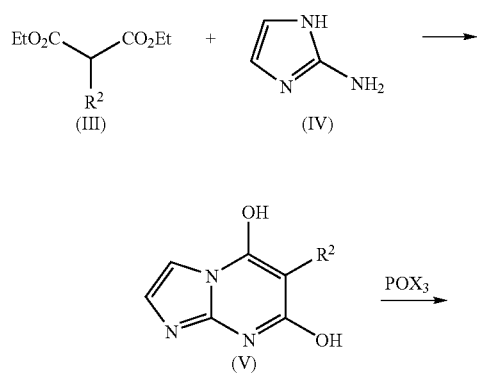

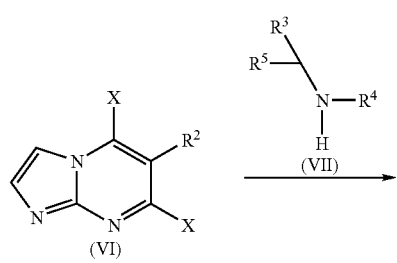

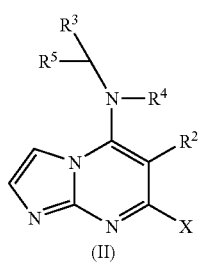

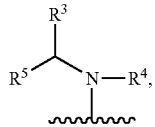

Compounds of Formulae (I) and (II) in which R¹ is $$R^5 \overset{R^3}{\underset{\text{wwww}}{-}} N-R^4,$$

Y represents a —O(CH₂)ₙQ group can be alternatively prepared as shown in Scheme II by reaction of (VIII) by replacing L⁵, which is a removable leaving group, in particular a fluorine atom, with an alcohol of Formula (IX) in the presence of a strong base including alkali metal hydroxide, alkali metal carbonate and alkali hydride, e.g., sodium hydride, in suitable solvents. Suitable solvents include aprotic solvents, such as dimethylsulfoxide, dimethylformamide, and the like. The reaction is suitably carried out at a temperature in the range from about 0° C. to about 100° C. to provide (X), a compound of formulae (I) and (II) in which Y represents a —O(CH₂)ₙQ group.

Scheme II:

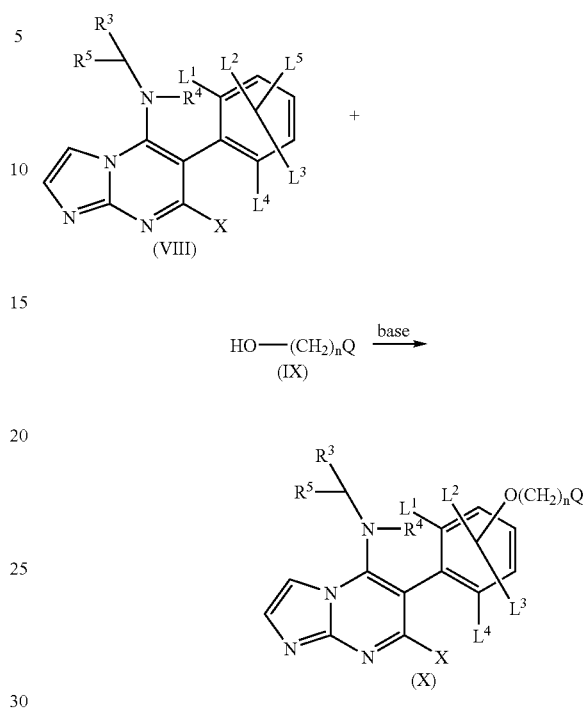

Compounds of Formulae (I) and (II) in which R¹ is C₆-C₈ cycloalkyl group can be prepared as shown in Scheme III-VI. As described in scheme III, ester (XI) is reacted with acid chloride (XII), prepared from the corresponding carboxylic acid where R¹ is C₆-C₈ cycloalkyl, in the presence of lithium diisopropylamide (LDA) to give ketone (XIII) which is further reacted with 2-aminoimidazole (IV) under alkaline conditions, using tertiary amines, such as tributylamine, at a temperature up to 190° C., to give imidazo[1,2-a]pyrimidin-7-ol (XIV).

Scheme III:

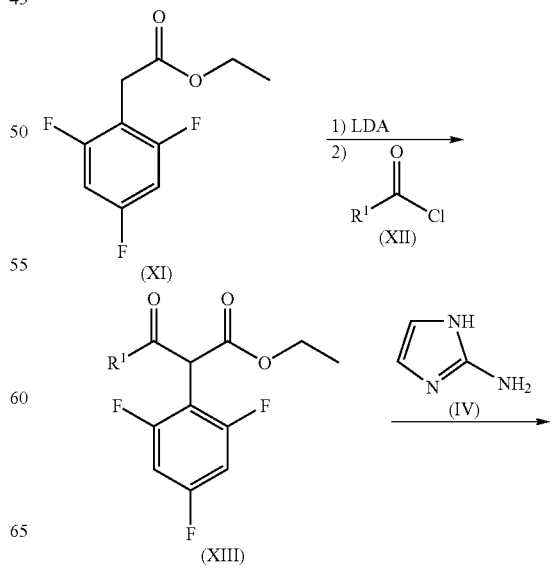

-continued

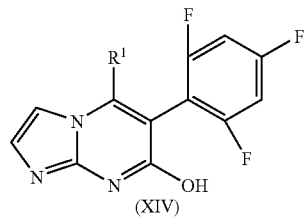

As shown in Scheme IV, imidazo[1,2-a]pyrimidin-7-ol (XIV) is reacted with alcohol (XV) in the presence of a strong base which includes an alkali metal hydroxide, alkali metal carbonate and alkali metal hydride, e.g., sodium hydride in an aprotic solvent which includes dimethylsulfoxide, dimethylformamide, and the like to give ether (XVI). Reaction of ether (XVI) with halogenating agents, $POX_3$ where X is Cl or Br such as phosphorous oxychloride or phosphorous oxybromide in the presence of N,N-diethylaniline affords compound (XVII) which is further reacted with 2,3-dichloro-5,6-dicyano-1,4-benzoquinone (DDQ) to afford ether (XVIII), a compound of formulae (I) and (II) where $R^1$ is $C_6$-$C_8$ cycloalkyl, Y is —$O(CH_2)_nQ$ and Q is OH.

Additionally, reaction of imidazo[1,2-a]pyrimidin-7-ol (XIV) with halogenating agents, $POX_3$ where X is Cl or Br such as phosphorous oxychloride or phosphorous oxybromide affords (XIX), a compound of formula (II) where $R^1$ is $C_6$-$C_8$ cycloalkyl, and Y is F.

Scheme IV:

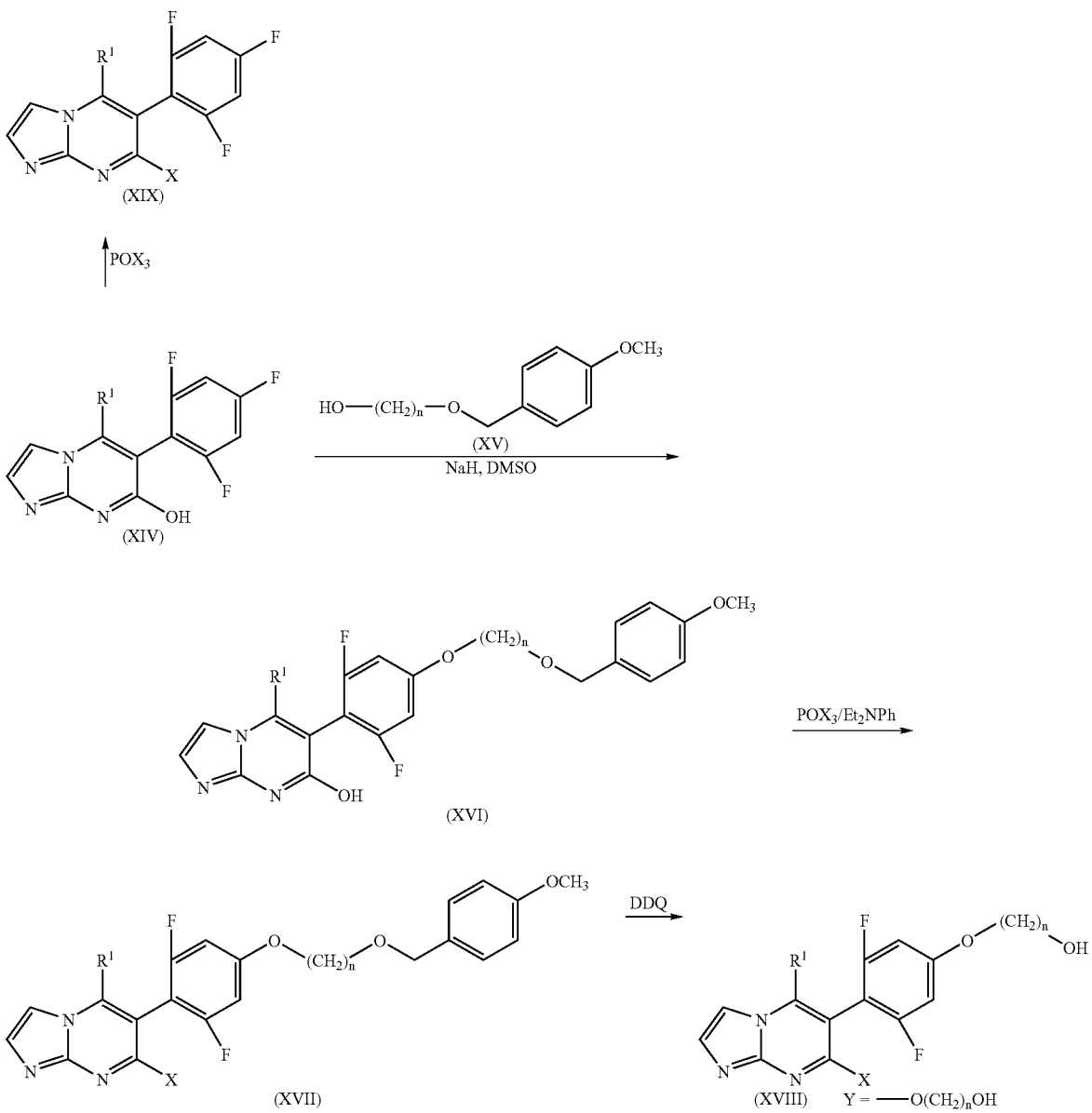

With reference to Scheme V, imidazo[1,2-a]pyrimidin-7-ol (XIV), where $R^1$ is $C_6$-$C_8$ cycloalkyl, is reacted with amino alcohol (XX), where $R^6$ and $R^7$ are other than H, in the presence of a strong base which includes an alkali metal hydroxide, alkali metal carbonate and alkali metal hydride, e.g., sodium hydride in the presence of an aprotic solvent which includes: dimethylformamide, dimethyl sulfoxide, and the like to give amine (XXI). Reaction of amine (XXI) with halogenating agents, $POX_3$ where X is Cl or Br such as phosphorous oxychloride or phosphorous oxybromide gives ether (XXII), a compound of formulae (I) and (II) where $R^1$ is $C_6$-$C_8$ cycloalkyl, Y is —$O(CH_2)_nQ$, Q is $NR^6R^7$ and $R^6$ and $R^7$ are other than H.

Scheme V:

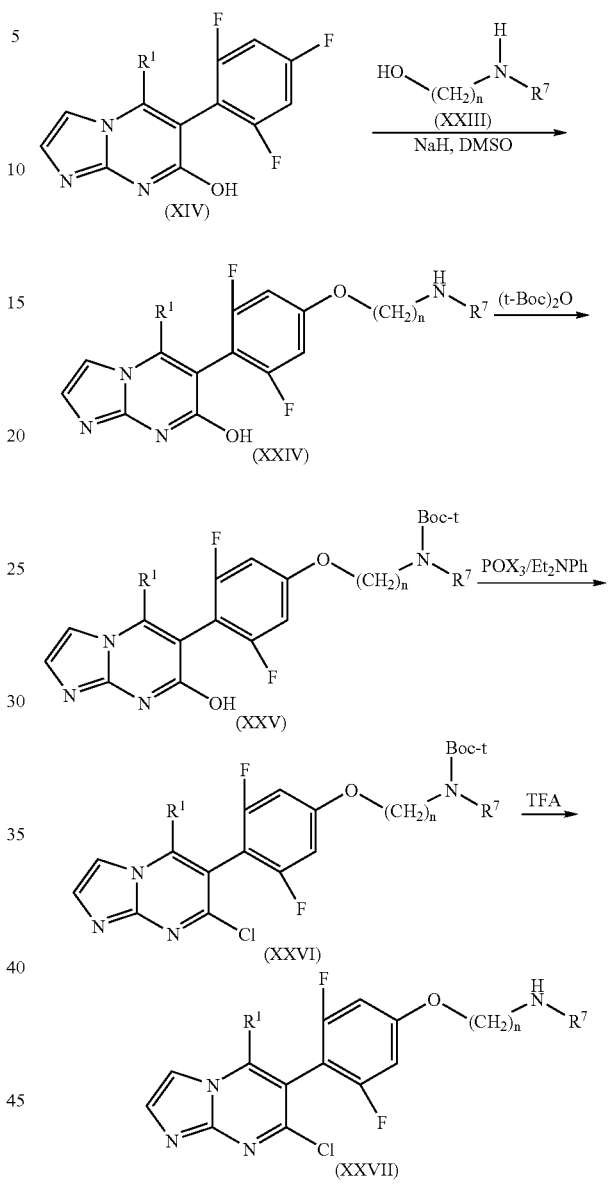

As shown in Scheme VI, imidazo[1,2-a]pyrimidin-7-ol (XIV), where $R^1$ is $C_6$-$C_8$ cycloalkyl, is reacted with amino alcohol (XXIII), where $R^6$ is H, in the presence of a strong base which includes an alkali metal hydroxide, alkali metal carbonate and alkali metal hydride, e.g., sodium hydride in the presence of an aprotic solvent which includes: dimethylformamide, dimethyl sulfoxide, and the like to give amine (XXIV). Protection of the nitrogen of amine (XXIV) by reaction with di-tert-butyl dicarbonate (t-Boc)$_2$O affords t-Boc protected amine (XXV) which is further reacted with halogenating agents, $POX_3$ where X is Cl or Br such as phosphorous oxychloride or phosphorous oxybromide in the presence of N,N-diethylaniline to afford halo compound (XXVI). Further reaction of halo compound (XXVI) with trifluoroacetic acid (TFA) affords amine (XXVII), a compound of formulae (I) and (II) where $R^1$ is $C_6$-$C_8$ cycloalkyl, Y is —$O(CH_2)_nQ$, Q is $NR^6R^7$ and $R^6$ is H.

Scheme VI:

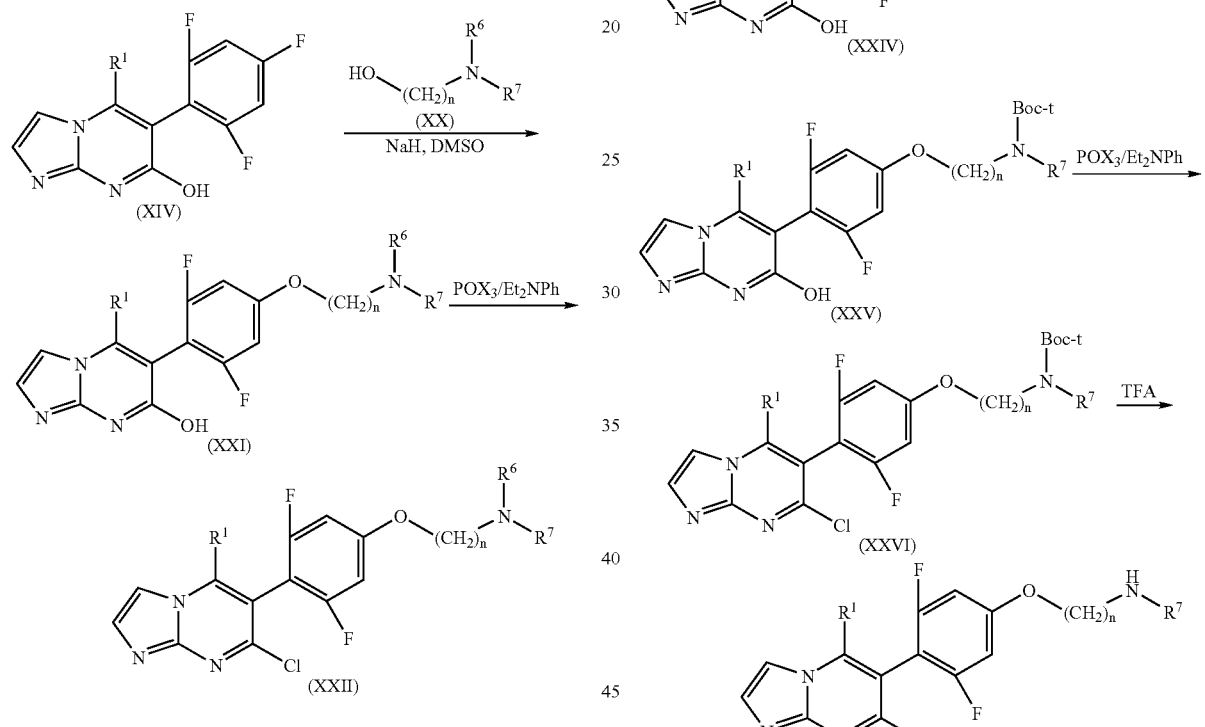

It is understood that this invention encompasses all crystalline and hydrated forms of compounds of Formulae (I) and (II) and their pharmaceutically acceptable salts. The pharmaceutically acceptable salts of the compounds of this invention are those derived from such organic and inorganic pharmaceutically acceptable salt forming acids as: lactic, citric, acetic, tartaric, fumaric, succinic, maleic, malonic, hydrochloric, hydrobromic, phosphoric, nitric, sulfuric, methanesulfonic, benzenesulfonic, L-aspartic, R or S-mandelic, palmitic and similarly known acceptable acids. A further salt is the trifluoroacetic acid salt (TFA). In particular the hydrochloride, fumarate and succinate salts are preferred.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier. Pharmaceutical compositions of this invention comprise compounds of Formula (I) or Formula (II).

Based on the results of standard pharmacological test procedures described herein, the compounds of this invention are useful as agents for treating, inhibiting or controlling the growth of cancerous tumor cells and associated diseases in a mammal in need thereof. The compounds of the invention are useful as agents for treating, inhibiting or controlling the growth of cancerous tumor cells and associated diseases in a mammal in need thereof by interacting with tubulin and microtubules and promoting microtubule polymerization. The compounds of the invention are also useful for the treatment or prevention of cancerous tumors that express multiple drug resistance (MDR) or are resistant because of MDR.

In particular, when contacting a tubulin containing system with an effective amount of a compound of formulae (I) or (II) results in the promotion of microtubule polymerization and further stabilizes microtubules and by promoting microtubule polymerization and stabilizing microtubules said compounds of formulae (I) or (II) are useful as agents for treating, inhibiting or controlling the growth of cancerous tumor cells and associated diseases. Additionally, compounds of formulae (I) or (II) are useful for the treatment or prevention of cancerous tumors that express multiple drug resistance (MDR) or are resistant because of MDR. The tubulin containing system may be in a tumor cell, thereby inhibiting neoplastic disease by administering an effective amount of a compound described in the present invention. Mammals may be treated and in particular, humans. Further, said tubulin containing system may be in a patient. In the case of cancer treatment, it is believed that many neoplasias such as leukemia, lung cancer, colon cancer, thyroid cancer, ovarian cancer, renal cancer, prostate cancer and breast cancers may be treated by effectively administering effective amounts of the compounds of formulae (I) or (II). As used herein, cancer refers to all types of cancers, or neoplasms or benign or malignant tumors. Preferred cancers for treatment using methods provided herein include carcinoma, sarcoma, lymphoma, or leukemia. By carcinoma is meant a benign or malignant epithelial tumor and includes, but is not limited to, breast carcinoma, prostate carcinoma, non-small lung carcinoma, colon carcinoma, melanoma carcinoma, ovarian carcinoma, or renal carcinoma. A preferred host is a human.

The effective dosage of active ingredient employed may vary depending on the particular compound employed, the mode of administration and severity of the condition being treated. However, in general satisfactory results are obtained when the compounds of the invention are administered in amounts ranging from about 0.10 to about 100 mg/kg of body weight per day. A preferred regimen for optimum results would be from about 1 mg to about 20 mg/kg of body weight per day and such dosage units are employed that a total of from about 70 mg to about 1400 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds of the invention may preferably be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

Intravenous administration is a preferred manner of administration of compounds of the invention. For intravenous administration examples of non-limiting suitable carriers include physiological saline, bacteriostatic water, Cremophor EL™ (BASF, Parsippany, N.J.) or phosphate buffered saline (PBS). The composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

As used in accordance with this invention, the term providing an effective amount of a compound means either directly administering such compound, or administering a prodrug, derivative, or analog which will form an effective amount of the compound within the body.

In addition to the above utilities some of the compounds of this invention are useful for the preparation of other compounds of this invention.

Examples of this invention are evaluated in several standard pharmacological test procedures that showed that the compounds of this invention possess significant activity as promoters of microtubule polymerization and are antineoplastic agents. Based on the activity shown in the standard pharmacological test procedures, the compounds of this invention are therefore useful as anticancer agents. Associated cancers are selected from the group consisting of breast, colon, lung, prostate, melanoma, epidermal, leukemia, kidney, bladder, mouth, larynx, esophagus, stomach, ovary, pancreas, liver, skin and brain. In particular, the compounds of this invention possess an effect similar to Paclitaxel. The test procedures used and results obtained are shown below.

Standard Pharmacological Test Procedures

Materials and Methods

Cell Culture Media and Reagents

Medium is RPMI-1640 with L-glutamine, supplemented with 10% heat-inactivated fetal calf serum, 100 units/mL penicillin, and 100 µg/mL streptomycin (Gibco, Grand Island, N.Y.). Microtubule-associated protein (MAP)-rich tubulin, containing about 70% tubulin and 30% MAPs (#ML113), and highly purified tubulin (>99% pure, #TL238), both from bovine brain, are obtained from Cytoskeleton, Inc., Denver, Colo. PEM buffer (80 mM piperazine-N,N'-bis[2-ethanesulfonic acid], pH 6.9, 1 mM ethylene glycol-bis(β-aminoethyl ether)-N,N,N',N'-tetraacetic acid, 1 mM magnesium chloride) and guanosine 5'-triphosphate (GTP) are also obtained from Cytoskeleton. [$^3$H]paclitaxel, specific activity 14.7 Ci/mmol, is purchased from Moravek Biochemicals (Brea, Calif.). [$^3$H]vinblastine, specific activity 9.60 Ci/mmol and MicroSpin G-50 columns are obtained from Amersham Biosciences (Piscataway, N.J.). [$^3$H]colchicine, specific activity 76.5 Ci/mmol, is obtained from New England Nuclear (Boston, Mass.). Other reagents are obtained from Sigma (St. Louis, Mo.).

Cell Lines

Human cancer cell lines, unless otherwise noted, are obtained from the American Type Culture Collection (Rockville, Md.). The following drug-sensitive parental cell lines, and their derived drug-resistant counterparts, are obtained from the originators as listed: (a) S1 (parental line from a subclone of human colon carcinoma line LS174T) and derived S1-M1-3.2 (herein called S1-M1) which expresses the MXR drug transporter protein, are provided by Dr. L. Greenberger, Wyeth Research (Rabindran, S. K., He, H., Singh, M., Brown, E., Collins, K. I., Annable, T., and Greenberger, L. M. Reversal of a novel multidrug resistance mechanism in human colon carcinoma cells by fumitremorgin C. Cancer Res., 58: 5850-5858,1998); (b) parental HL-60 human promyelocytic leukemia line and derived HL-60/ADR, which expresses the MRP1 drug transporter protein, are provided by Dr. M. Center, University of Kansas (McGrath, T., and Center, M. S. Adriamycin resistance in HL60 cells in the absence of detectable P-glycoprotein. Biochem. Biophys. Res. Commun., 145:1171-1176,1987), via Dr. L. Greenberger, Wyeth Research; and (c) parental KB-3-1 (herein called KB, cloned from a human epidermoid carcinoma) and the derived lines KB-8-5 and KB-V1, which express moderate and very high levels of the MDR1 (P-glycoprotein) drug transporter protein, respectively, are provided by Dr. M. Gottesman, National Cancer Institute (Shen, D. W., Cardarelli, C., Hwang, J., Cornwell, M., Richert, N., Ishii, S., Pastan, I., and Gottesman, M. M. Multiple drug-resistant human KB carcinoma cells independently selected for high-level resistance to colchicine, adriamycin, or vinblastine show changes in expression of specific proteins. J. Biol. Chem., 261: 7762-7770, 1986) via Dr. L. Greenberger, Wyeth Research.

Cytotoxicity Standard Pharmacological Test Procedures

Two different standard cytotoxicity assays are used: the "MTS" assay, and the "SRB" assay.

The MTS assay, which is sold in kit form by Promega (Madison, Wis.; CellTiter 96 AQueous Non-Radioactive Cell Proliferation Assay), is based on the conversion by viable cells, but not by dead cells, of the tetrazolium salt, MTS (3-(4,5-dimethylthiazol-2-yl)-5-(3-carboxymethoxyphenyl)-2-(4-sulphophenyl)-2H-tetrazolium, inner salt), into a water-soluble colored formazan which is detected by spectrophotometry. Compounds are tested at nine concentrations, in order to determine $IC_{50}$ values. For the test procedure, cells are harvested by trypsinization (or, in the case of non-adherent cells, by simple resuspension), washed, counted and distributed to wells of 96-well flat-bottom microtiter plates at 1000 cells per well in 200 µL of medium. In addition, one row of wells on a separate plate receives cells as above ("time 0" plate). All plates are incubated at 370 in humidified 5% $CO_2$ in air for about 24 hr.

On day 2, compounds for test are diluted and added to wells. Compounds are dissolved in DMSO at 10 mg/mL. For each compound, nine serial 2-fold dilutions are prepared in DMSO. Ten µL of each dilution in DMSO is transferred to 100 µL of medium, mixed well, and then 5 µL of this dilution is transferred in quadruplicate to wells containing cells. The final high concentration of each compound is typically 1-5 µM. Plates are returned to the incubator for three days. At the time of drug addition to the experimental plates, the MTS assay is run on the "time 0" plate. This gives the "time 0 MTS value" which is related to the number of viable cells per well at the time of drug addition.

After three days of culture with test compounds (day 5 overall), the MTS assay is done on all wells of the experimental plates. The absorbance values of the quadruplicate sample wells are averaged and divided by the average of the "time 0" values. The average of control wells without drug, divided by the average "time 0" value, gives the maximal relative increase in MTS color yield due to cell growth during the final three days of culture. The average of control wells with high drug concentration, divided by the "time 0" value, gives the minimal relative color yield for cells that were completely killed. The nine values for each compound are plotted against concentration, and the concentration that produces a relative color yield half way between the maximum and minimum is taken as the $IC_{50}$ value. The most potent compounds have the lowest $IC_{50}$ values.

The SRB standard cytotoxicity assay is done according to previously reported methods (Discafani, C. M., Carroll, M. L., Floyd Jr., M. B. F., Hollander, I. J., Husain, Z., Johnson, B. D., Kitchen, D., May, M. K., Malo, M. S., Minnick Jr., A. A., Nilakantan, R., Shen, R., Wang Y-F., Wissner, A., Greenberger, L. M. Irreversible inhibition of epidermal growth factor receptor tyrosine kinase with in vivo activity by N-[4-[3-bromophenyl)amino]-6-quinaxolinyl]-2-butynamide (CL-387,785). Biochem. Pharmacol., 57: 917-925, 1999). Briefly, cells are plated in 100 µL of medium in 96-well flat-bottom microtiter plates in the morning of day 1 and allowed to adhere to the plates for 2-6 hr. Compounds are serially diluted into medium as 2× stocks and 100 µL of these stocks are added to cells in duplicate. Compounds are incubated with cells for 3 days. At the end of the incubation period the sulforhodamine B (SRB) assay, which measures protein content as an assessment of cell survival, is performed as described previously (Skehan, P., Storeng, R., Scudiero, D., Monks, A., McMahon, J., Vistica, D., Warren, J. T., Bokesch, H., Kenney, S., Boyd, M. R. New calorimetric cytotoxicity assay for anticancer-drug screening. J. Natl. Cancer Inst., 82:1107-1112, 1990) with some modifications. Medium is gently decanted from plates and replaced with 200 µL per well of cold serum-free medium containing a final concentration of 10% trichloroacetic acid. The plates are incubated for 1 hr at 40, washed 5 times in cold distilled water, and air-dried overnight. The fixed cells are stained for 10 min with 80 µL per well of 0.04% SRB solution prepared in 1% glacial acetic acid. Staining solution is decanted, plates are washed 5 times in 1% glacial acetic acid, and then air-dried until completely dry. Stained cell product is dissolved in 150 µL per well of 10 mM Trizma Base with shaking for 20 minutes. Absorbance is read on a Victor V multi-label plate reader (Perkin Elmer, Gaithersburg, Md.).

Tubulin Polymerization Standard Pharmacological Test Procedure

Two variations of this procedure are done, one using MAP-rich tubulin and one using pure tubulin.

MAP-rich tubulin is dissolved in ice-cold PEM buffer containing 1 mM GTP (GPEM buffer) at a concentration of 1.3 mg/mL. The solution is centrifuged at top speed in an Eppendorf model 5415C microcentrifuge (Brinkmann Instruments, Westbury, N.Y.) for 10 min at 40 immediately before use. The tubulin solution is added to wells of a ½-area 96-well plate (Costar No. 3696, Corning, Inc., Corning, N.Y.) already containing the compounds of interest. Each compound is tested in duplicate at a final concentration of 0.3 µM in a volume of 110 µL per well. The final DMSO concentration in all wells is 0.3%. Control reactions, which receive compound solvent only, are done in quadruplicate. The plate is put in a SpectraMax Plus plate reader (Molecular Devices Corp. Sunnyvale, Calif.) thermostated at 240 and the absorbance of each well at 340 nm, a measure of the appearance of turbidity due to tubulin polymer formation, is determined every minute for 60 minutes. The absorbance at time 0 for each well is subtracted from each of the subsequent absorbance readings for that well, and then the duplicates are averaged.

The procedure with pure tubulin is similar except for the following changes. Pure tubulin is dissolved in cold PEM buffer containing 10% glycerol and no added GTP at a concentration of 1.5 to 1.8 mg/mL (15 to 18 µM). The supernatant after centrifugation is dispensed to a ½-area 96-well plate already containing compounds. Each compound is tested in duplicate at a final concentration of 24.3 µM. The plate reader µs thermostated at 35°.

Competitive Binding Standard Pharmacological Test Procedure

The binding of examples of this invention to highly purified tubulin is studied by competitive inhibition methods. The αβ-tubulin heterodimer contains binding sites for the three major classes of microtubule-active pharmacological agents: taxanes, vinca/peptide-site agents, and colchicine-site agents. To study possible competition at the vinca/peptide and colchicine sites, incubations are done under conditions which do not favor polymerization because vinblastine and colchicine bind preferentially to unpolymerized heterodimer. To study possible competition at the taxane site, on the other hand, polymerized tubulin (microtubules) is used because paclitaxel binds preferentially to microtubules.

Highly purified tubulin is dissolved in PEM buffer without GTP and used at a final concentration of 1.0 to 1.3 mg/ml (10 to 13 µM). To aliquots of the tubulin solution are added various competitors (in quadruplicates) at 100 µM final concentrations, and [$^3$H]vinblastine or [$^3$H]colchicine at final concentrations of 100 nM or 50 nM, respectively. These solutions are incubated at 240 for 1 hr and then applied to MicroSpin G-50 columns which are centrifuged for 2 min at 3000 rpm in an Eppendorf 5415C microfuge. An aliquot of each column effluent (containing tubulin and bound radioligand) is mixed with scintillation fluid and counted in a liquid scintillation spectrometer. Controls include samples without competitor, and samples with unlabeled vincristine, colchicine, or paclitaxel. Quadruplicates are averaged, and the ability of the competitor to inhibit the binding of the radioligand is expressed as a percentage of control binding in the absence of any competitor.

For competition with [$^3$H]paclitaxel, highly purified tubulin is dissolved in PEM buffer containing 0.75 M glutamate and 25 µM dideoxy-GTP; final protein concentration is 0.25 to 0.35 mg/mL (2.5 to 3.5 µM). These conditions foster the rapid formation of short, stable microtubule polymers (Hamel, E., del Campo, A. A., and Lin, C. M. Stability of tubulin polymers formed with dideoxyguanosine nucleotides in the presence and absence of microtubule-associated proteins. J. Biol. Chem., 259: 2501-2508, 1984). This solution is incubated for 30 min at 370 to allow microtubules to form. Then [$^3$H]paclitaxel (final concentration of 2.1 µM, 1.2 Ci/mmol) and competitor (final concentration of 20 µM, except 5 µM for unlabeled paclitaxel) are added to aliquots of the polymerized tubulin solution and incubation at 370 is continued for another 30 min. Controls include samples without competitor, and samples with unlabeled vincristine, colchicine, or paclitaxel. The reactions are then centrifuged at top speed in an Eppendorf 5415C microfuge for 20 min at room temperature in order to pellet the microtubule protein. Triplicate aliquots of each supernatant are mixed with scintillation fluid and counted in a liquid scintillation spectrometer. From the amount of radioactivity in the supernatants and the measured total starting radioactivity, the amount of [$^3$H]paclitaxel bound to pelleted microtubule protein is calculated. The ability of each competitor to inhibit radioligand binding to pelleted protein is expressed as a percent of controls without any competitor.

Results

1. Cytotoxicity Standard Pharmacological Test Procedure 1.1. With COLO 205 Cells COLO 205 is a human colon carcinoma cell line that is used for comparative testing of the examples of this invention and several reference compounds (Table 1). This line is sensitive to paclitaxel and vincristine.

TABLE 1

Activity of Examples of the Invention and Reference Compounds in the MTS Cytotoxicity Standard Pharmacological Test Procedure with COLO 205 Cells[1]

| Example or Reference Compound | $IC_{50}$ (nM) | SD | n |
|---|---|---|---|
| 1 | 259 | 74 | 3 |
| 2 | 396 | 8 | 2 |
| 3 | 742 | 385 | 2 |
| 4 | 88 | 26 | 2 |
| 5 | 207 | 111 | 2 |
| 6 | 45 | 17 | 3 |
| Paclitaxel | 3.3 | 1.0 | 20 |
| Vincristine | 2.6 | 0.5 | 7 |

[1]$IC_{50}$ values and standard deviations are from the indicated number of independent experiments 1.2. With KB, KB-8-5, and KB-V1 Cells The KB lines express different amounts of the P-glycoprotein (MDR1) membrane pump which produces resistance to the action of many cytotoxic compounds, including paclitaxel and vincristine. The parental KB line expresses no P-glycoprotein, KB-8-5 expresses moderate levels of the protein, and KB-V1 expresses very high levels. The ability of P-glycoprotein to recognize and export a potential cytotoxic agent can be inferred from the change in $IC_{50}$ values on these lines (Loganzo, F., Discafani, C. M., Annable, T., Beyer, C., Musto, S., Hari, M., Tan, X., Hardy, C., Hernandez, R., Baxter, M., Singanallore, T., Khafizova, G., Poruchynsky, M. S., Fojo, T., Nieman, J. A., Ayral-Kaloustian, S., Zask, A., Andersen, R. J., and Greenberger, L. M. HTI-286, a synthetic analogue of the tripeptide hemiasterlin, is a potent antimicrotubule agent that circumvents P-glycoprotein-mediated resistance in vitro and in vivo. Cancer Res., 63: 1838-1845, 2003). If a compound is recognized by P-glycoprotein, its $IC_{50}$ value will increase substantially (several hundred-fold) on going from KB to KB-8-5 or KB-V1; if a compound is not recognized, it will have similar $IC_{50}$ values (3-fold or less difference) on all three lines. For example, as shown in Table 2, KB-8-5 cells are moderately resistant to paclitaxel (19-fold), vincristine (11-fold), colchicine (3.4-fold) and doxorubicin (3.0-fold). In contrast, example 6 of this invention shows a 1.4-fold change in $IC_{50}$ values. In addition, example 4, tested in the SRB cytotoxicity assay procedure (Table 3), has a ratio of 2.5 compared with a ratio of 16 for paclitaxel.

Even slight interactions of compounds with P-glycoprotein can be determined with the KB-V1 line, which expresses a level of this protein higher than is typically found in clinical samples from a variety of tumors (Goldstein, L. J., Galski, H., Fojo, T., Willingham, M., Lai, S. L., Gazdar, A., Pirker, R., Green, A., Crist, W., Brodeur, G. M., Lieber, M., Cossman, J., Gottesman, M. M., and Pastan, I. Expression of a multidrug resistance gene in human cells. J. Natl. Cancer Inst. (Bethesda), 81: 116-124, 1989). KB-V1 cells are highly resistant to paclitaxel (>345-fold), vincristine (>156-fold), colchicine (116-fold), mitoxantrone (77-fold), and doxorubicin (>130-fold). Example 6 of this invention shows a 4.6-fold change in $IC_{50}$ compared to the parental KB line (Table 2). This indicates that example 6 is barely recognized by P-glycoprotein and therefore that it overcomes P-glycoprotein-mediated resistance to cell killing. Example 4, tested in the SRB cytotoxicity assay procedure (Table 3), has a ratio of 99 compared with a ratio of >1,360 for paclitaxel in the same assay, indicating that although example 4 shows greater recognition by P-glycoprotein than example 6, it too is recognized much less than paclitaxel.

TABLE 2

Activity of Example 6 of the Invention and Reference Compounds in the MTS Cytotoxicity Standard Pharmacological Test Procedure with KB, KB-8.5 and KB-VI Cells

| Example or Reference Compound | $IC_{50}$ (nM)[1] | | | Ratio[2] | |
|---|---|---|---|---|---|
| | KB | KB 8.5 | KB VI | 8.5/KB | VI/KB |
| 6 | 44 | 63 | 204 | 1.4 | 4.6 |
| Paclitaxel | 2.9 | 56 | >1,000 | 19 | >345 |
| Vincristine | 6.4 | 72 | >1,000 | 11 | >156 |
| Colchicine | 18 | 59 | 2,038 | 3.4 | 116 |
| Camptothecin | 24 | 33 | 39 | 1.4 | 1.6 |
| Mitoxantrone | 25 | 27 | 1,927 | 1.1 | 77 |
| Doxorubicin | 23 | 70 | >3,000 | 3.0 | >130 |

[1]$IC_{50}$ values are means of 2 independent experiments.
[2]Ratio = $IC_{50}$ on KB 8.5 or KB VI cells/$IC_{50}$ on KB cells. A ratio of about 1 indicates no resistance.

TABLE 3

Activity of Example 4 of the Invention and Paclitaxel in the SRB Cytotoxicity Standard Pharmacological Test Procedure with KB, KB-8.5 and KB-VI Cells

| Example or Reference Compound | $IC_{50}$ (nM)[1] | | | Ratio[2] | |
|---|---|---|---|---|---|
| | KB | KB 8.5 | KB VI | 8.5/KB | VI/KB |
| 4 | 24 | 59 | 2387 | 2.5 | 99 |
| Paclitaxel | 2.2 | 34 | >3000 | 16 | >1360 |

[1]$IC_{50}$ values are means of 2 independent experiments.
[2]Ratio = $IC_{50}$ on KB 8.5 or KB VI cells/$IC_{50}$ on KB cells. A ratio of about 1 indicates no resistance.

1.3. With HL-60 and HL-60/ADR Cells

HL-60/ADR cells overexpress the multidrug resistance protein MRP1 which mediates resistance to some chemotherapeutics (Gottesman, M. M., Fojo, T., and Bates, S. E. Multidrug resistance in cancer: role of ATP-dependent transporters. Nature Rev. Cancer, 2: 48-58, 2002). The $IC_{50}$ values of example 6 of this invention, as well as reference compounds, on HL-60/ADR are compared to values on the sensitive parental HL-60 line. The results, shown in Table 4, indicate that whereas HL-60/ADR cells show resistance to vincristine (8.2-fold), colchicine (7.4-fold), mitoxantrone (17-fold), and doxorubicin (93-fold), these cells show no resistance to example 6. This indicates that example 6 is not recognized by MRP1 and therefore overcomes cellular resistance mediated by this transporter.

TABLE 4

Activity of Example 6 of the Invention and Reference Compounds in the MTS Cytotoxicity Standard Pharmacological Test Procedure with HL-60 and HL-60/ADR Cells

| Example or Reference Compound | $IC_{50}$ (nM)[1] HL-60 | HL-60/ADR | Ratio[2] |
|---|---|---|---|
| 6 | 53 | 29 | 0.55 |
| Paclitaxel | 5.7 | 6.4 | 1.1 |
| Vincristine | 2.5 | 20 | 8.2 |
| Colchicine | 9.3 | 69 | 7.4 |
| Camptothecin | 12 | 17 | 1.4 |
| Mitoxantrone | 9.5 | 161 | 17 |
| Doxorubicin | 23 | 2,085 | 93 |

[1]$IC_{50}$ values are means of 2 independent experiments.
[2]Ratio = $IC_{50}$ on HL-60/ADR cells/$IC_{50}$ on HL-60 cells. A ratio of about 1 indicates no resistance.

1.4. With S1 and S1-M1 Cells

S1-M1 cells overexpress the MXR transporter which mediates resistance to some chemotherapeutics (Gottesman, M. M., Fojo, T., and Bates, S. E. Miltidrug resistance in cancer: role of ATP-dependent transporters. Nature Rev. Cancer, 2: 48-58, 2002). The $IC_{50}$ values of example 6 of this invention, as well as reference compounds, on S1-M1 are compared to values on the sensitive parental S1 line. The results, shown in Table 5, indicate that whereas S1-M1 cells show resistance to mitoxantrone (>300-fold) and doxorubicin (74-fold), they show no resistance to example 6. This indicates that example 6 is not recognized by MXR and therefore overcomes cellular resistance mediated by this transporter.

TABLE 5

Activity of Example 6 of the Invention and Reference Compounds in the MTS Cytotoxicity Standard Pharmacological Test Procedure with S1 and S1-M1 Cells

| Example or Reference Compound | $IC_{50}$ (nM)[1] S1 | S1-M1 | Ratio[2] |
|---|---|---|---|
| 6 | 63 | 68 | 1.1 |
| Paclitaxel | 8.1 | 4.4 | 0.54 |
| Vincristine | 5.6 | 4.6 | 0.82 |
| Colchicine | 18 | 60 | 3.3 |
| Camptothecin | 8.9 | 17 | 1.9 |
| Mitoxantrone | 10 | >3,000 | >300 |
| Doxorubicin | 34 | 2,517 | 74 |

[1]$IC_{50}$ values are means of 2 independent experiments.
[2]Ratio = $IC_{50}$ on S1-M1 cells/$IC_{50}$ on S1 cells. A ratio of about 1 indicates no resistance.

2. Effects of Compounds on Polymerization of MAP-rich and Pure Tubulin in vitro In this assay, control reactions with MAP-rich tubulin show an S-shaped absorbance profile characterized by three phases: first, a lag phase during which no change in absorbance occurs; second, a polymerization phase in which absorbance increases; and third, a plateau phase in which absorbance has reached a maximum and little or no further change occurs. Polymerization enhancers such as paclitaxel and docetaxel shorten or eliminate the lag phase, increase the rate of the polymerization phase, and often increase the height of the plateau. Polymerization inhibitors such as vincristine and colchicine reduce or prevent the absorbance increase. Example 6 of this invention has a taxane-like effect on the polymerization reaction. This has been expressed quantitatively in Table 6 by dividing the mean A340 of each sample at 20 min by the mean A340 of the control at 20 min to give a fold enhancement over control. Paclitaxel and docetaxel show enhancement factors of 1.8 and 5.4, respectively. Example 6 of this invention has an enhancement factor of 1.7. In contrast, vincristine has an enhancement factor of 0.5 because it partially inhibits polymerization of MAP-rich tubulin.

TABLE 6

Activity of Example 6 of the Invention and Reference Compounds in the Tubulin Polymerization Standard Pharmacological Test Procedure with MAP-rich Tubulin

| Example or Reference Compound | $A_{340}$ Compound / $A_{340}$ Control |
|---|---|
| 6 | 1.7 |
| Paclitaxel | 1.8 |
| Docetaxel | 5.4 |
| Vincristine | 0.5 |
| Control | 1.0 |

Pure tubulin without added GTP shows no polymerization in control reactions. Docetaxel and paclitaxel are able to induce polymerization of pure tubulin under these conditions. Example 6 of this invention also induces polymerization of pure tubulin without GTP in a manner similar to docetaxel. Table 7 shows the mean absorbance at four time points after the start of the reactions for a single compound concentration. At this concentration (24.3 µM) docetaxel and example 6 cause a rapid increase in absorbance within the first 5 min of reaction to a plateau. The microtubule destabilizers vincristine and colchicine show no activity in this assay.

TABLE 7

Activity of Example 6 of the Invention and Reference Compounds in the Tubulin Polymerization Standard Pharmacological Test Procedure with Pure Tubulin

| Example or Reference Compound | $A_{340}$ at 0 min | 5 min | 10 min | 15 min | 20 min |
|---|---|---|---|---|---|
| 6 | 0 | 0.15 | 0.19 | 0.19 | 0.19 |
| Docetaxel | 0 | 0.20 | 0.20 | 0.20 | 0.20 |
| Vincristine | 0 | 0.01 | 0.01 | 0 | 0 |
| Colchicine | 0 | 0 | 0 | 0 | 0 |
| Control | 0 | 0 | 0 | 0 | 0 |

Binding of Compounds to Tubulin

The site on highly purified bovine brain tubulin to which compounds of this invention bind is determined by competitive inhibition studies with the radioactive ligands [$^3$H]vinblastine, [$^3$H]colchicine, and [$^3$H]paclitaxel. The results, shown in Table 8, indicate that example 6 inhibits the binding of [$^3$H]vinblastine to tubulin heterodimer (17% of control), but does not inhibit binding of [$^3$H]colchicine to tubulin heterodimer or of [$^3$H]paclitaxel to microtubules. This is strong evidence that this example binds at the vinca/peptide site of tubulin and not at the colchicine or taxane sites. Among the control compounds tested, vincristine inhibited [$^3$H]vinblastine binding but not [$^3$H]colchicine, and colchicine inhibited [$^3$H]colchicine binding but not [$^3$H]vinblastine. Vincristine and colchicine also appear to inhibit the binding of [$^3$H]paclitaxel to microtubules; however, this is not due to binding competition but rather to depolymerization of the microtubules to which [$^3$H]paclitaxel binds. It is clear that example 6 of this invention does not reduce [³H]paclitaxel binding to microtubules, which indicates that it neither competes with [³H]paclitaxel for binding nor depolymerizes the microtubules to which [³H] paclitaxel binds.

TABLE 8

Activity of Example 6 of the Invention and Reference Compounds in the Competitive Binding Standard Pharmacological Test Procedure[1]

| | Radioactive Ligand | | | | | |
|---|---|---|---|---|---|---|
| | [³H]Vinblastine | | [³H]Colchicine | | [³H]Paclitaxel | |
| Competitor | Mean[2] | SD[2] | Mean[2] | SD[2] | Mean[3] | SD[3] |
| Control | 100 | | 100 | | 100 | |
| Example 6 | 17 | 1.7 | 84 | 3.5 | 92 | 6.5 |
| Vincristine | 5 | 1.0 | 99 | 7.9 | 22 | 0.9 |
| Colchicine | 125 | 12.6 | 6 | 1.9 | 19 | 0.2 |
| Paclitaxel | 92 | 7.8 | 93 | 12.3 | 35 | 1.6 |

[1]Results are expressed as percent of binding to control without competitor.
[2]Data are from 1 (4 replicates) or 2 (8 replicates) independent experiments.
[3]Data are from 1 to 4 independent experiments (3 to 12 replicates).

Compounds of this invention show potent cytotoxic activity against multiple human cancer cell lines in culture, including lines that are resistant to paclitaxel and vincristine because of drug transporter overexpression. The compounds enhance the initial rate of MAP-rich tubulin polymerization, in a manner reminiscent of taxanes and distinct from the inhibitory effects of depolymerizers such as vinca alkaloids and colchicine. They also induce polymerization of pure tubulin in the absence of GTP. Compounds of this invention bind to the vinca/peptide site of tubulin.

The following examples further illustrate the present invention. It should be understood, however, that the invention is not limited solely to the particular examples given below.

EXAMPLE 1

Preparation of 5-azepan-1-yl-7-chloro-6-(2,4,6-trifluorophenyl)imidazo[1,2-a]pyrimidine

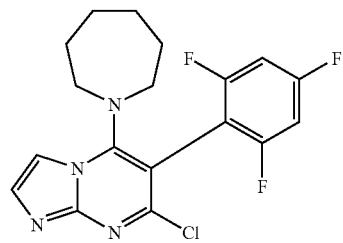

Step A: 5,7-dichloro-6-(2,4,6-trifluorophenyl)imidazo[1,2-a]pyrimidine

A mixture of diethyl 2-(2,4,6-trifluorophenyl)malonate (U.S. Pat. No. 6,156,925) (870 mg, 3.0 mmol), 2-aminoimidazole (Hel. Acta. Chim. 76, 2066 (1993)) (274 mg, 3.3 mmol), and 1.0 mL of tributylamine is stirred under nitrogen atmosphere at 160° C. for 0.5 h and cooled to room temperature. The mixture is dissolved in ethyl acetate and the organic layer is washed with 1.0 N hydrochloric acide (×3) and saturated sodium chloride, dried over magnesium sulfate, and concentrated. The residue is dissolved in ethyl acetate (5 mL) and to this solution is added hexanes (50 mL). The precipitates are collected by filtration, washed with hexanes to give 6-(2,4,6-trifluorophenyl)imidazo[1,2-a]pyrimidine-5,7-diol as a tan solid (180 mg). MS: m/z 279.9 (M−H).

A mixture of 6-(2,4,6-trifluorophenyl)imidazo[1,2-a]pyrimidine-5,7-diol (180 mg) in 1 mL of phosphorous oxychloride is heated at reflux for 6 h. The excess phosphorous oxychloride is removed in vaccuo, and the resulting residue is dissolved in methylene chloride. The organic layer is washed with water, dried over magnesium sulfate, and concentrated. The residue is chromatographed over silica gel, eluting with a gradient of 10% ethyl acetate in hexanes to 33% ethyl acetate in hexanes. Concentration provides 5,7-dichloro-6-(2,4,6-trifluorophenyl)imidazo[1,2-a]pyrimidine as a white solid (62 mg). MS: m/z 318.0 (M+H).

Step B: 5-Azepan-1-yl-7-chloro-6-(2,4,6-trifluorophenyl)imidazo[1,2-a]pyrimidine A solution of 5,7-dichloro-6-(2,4,6-trifluorophenyl)imidazo[1,2-a]pyrimidine (16 mg, 0.05 mmol) and hexamethyleneimine (100 mg, 1.0 mmol) in 1 mL of methylene chloride is stirred at room temperature for 16 h. The organic solution is washed with 0.1 N hydrochloric acid and saturated sodium chloride, dried over magnesium sulfate, and concentrated. The residue is chromatographed over silica gel, eluting with a gradient of 20% ethyl acetate in hexanes to 50% ethyl acetate in hexanes. Concentration provides 5-azepan-1-yl-7-chloro-6-(2,4,6-trifluorophenyl)imidazo[1,2-a]pyrimidine as a yellow solid (15 mg, mp 106-108° C.). MS: m/z 381.0 (M+H).

Example 2 is synthesized analogously to Example 1.

EXAMPLE 2

7-Chloro-5-piperidin-1-yl-6-(2,4,6-trifluorophenyl)imidazo[1,2-a]pyrimidine; MS: m/z 367.3(M+H)

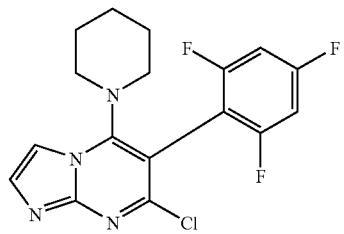

EXAMPLE 3

Preparation of 7-chloro-N-(2,2,2-trifluoroethyl)-6-(2,4,6-trifluorophenyl)imidazo[1,2-a]pyrimidin-5-amine;

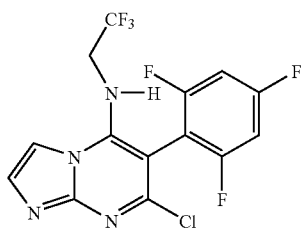

A solution of 5,7-dichloro-6-(2,4,6-trifluorophenyl)imidazo[1,2-a]pyrimidine (16 mg, 0.05 mmol) and 2,2,2-trifluoroethylamine (200 mg, 2.0 mmol) in 1 mL of N,N-dimethylformamide is stirred at room temperature for 16 h. A saturated sodium chloride solution is added, and the product is extracted with ethyl acetate. The organic solution is washed with saturated sodium chloride, dried over magnesium sulfate, and concentrated. The residue is chromatographed over silica gel, eluting with a gradient of 20% ethyl acetate in hexanes to 50% ethyl acetate in hexanes. Concentration provides 7-chloro-N-(2,2,2-trifluoroethyl)-6-(2,4,6-trifluorophenyl)imidazo[1,2-a]pyrimidin-5-amine as a white solid (16 mg, mp 155-157° C.). MS: m/z 381.0 (M+H).

EXAMPLE 4

Preparation 7-chloro-6-{4-[3-(dimethylamino)propoxy]-2,6-difluorophenyl}-N-(2,2,2-trifluoroethyl)imidazo[1,2-a]pyrimidin-5-amine;

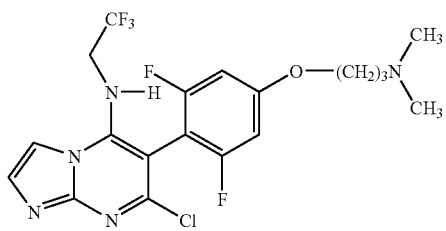

To a solution of 7-chloro-N-(2,2,2-trifluoroethyl)-6-(2,4,6-trifluorophenyl)imidazo[1,2-a]pyrimidin-5-amine (19 mg, 0.05 mmol) and 3-dimethylamino-1-propanol (51 m g, 0.5 mmol) in 0.5 mL of dimethylsulfoxide at room temperature is added sodium hydride (60% in mineral oil, 20 mg, 0.5 mmol). The mixture is heated at 50° C. for 30 minutes, and cooled to room temperature. A saturated sodium chloride solution is added, and the product is extracted with ethyl acetate. The organic solution is washed with saturated sodium chloride (×3), dried over magnesium sulfate, and concentrated. The residue is chromatographed over silica gel, eluting with a gradient of ethyl acetate to 30% methyl alcohol in ethyl acetate. Concentration provides 7-chloro-6-{4-[3-(dimethylamino)propoxy]-2,6-difluorophenyl}-N-(2,2,2-trifluoroethyl)imidazo[1,2-a]pyrimidin-5-amine as a tan solid (12 mg, mp 52-55° C.). MS: m/z 464.3 (M+H).

EXAMPLE 5

7-Chloro-5-cycloheptyl-6-(2,4,6-trifluorophenyl)imidazo[1,2-a]pyrimidine;

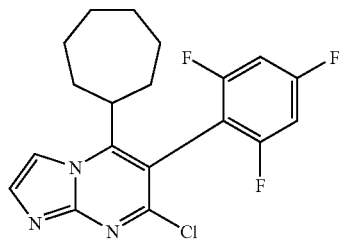

Step A: Ethyl 3-cycloheptyl-3-oxo-2-(2,4,6-trifluorophenyl)propanoate

A mixture of 2,4,6-trifluorophenylacetic acid (570 mg, 3.0 mmol), iodoethane (1.56 g, 10 mmol), and potassium carbonate (1.38 g, 10 mmol) in 5 mL of dimethylsulfoxide is stirred at 50° C. for 3 h, and cooled to room temperature. The mixture is partitioned between diethyl ether and water. The organic layer is washed with water, and saturated sodium chloride, dried over magnesium sulfate, and filtered through magnesol. The filtrate is concentrated to give ethyl 2,4,6-trifluorophenylacetate as a light yellow oil (581 mg, 2.66 mmol).

A mixture of cycloheptanecarboxylic acid (5.0 g, 35.2 mmol) in 25 mL of thionyl chloride is refluxed for 1 h, and concentrated. The crude cycloheptanecarboxylic acid chloride thus obtained is used directly in the next step.

A solution of ethyl trifluorophenylacetate (436 mg, 2.0 mmol) in 3 mL of tetrahydrofuran is cooled to −78° C., and lithium diisopropylamide (2.0 M in heptane/tetrahydrofuran/ethylbenzene, 1.0 mL, 2.0 mmol) is added dropwise with stirring. The mixture is stirred at −78° C. for 1 h, and cycloheptanecarboxylic acid chloride (321 mg, 2.0 mmol) is added dropwise. The mixture is warmed to room temperature and acidified with 2 mL of 1.0 N hydrochloric acid. The product is extracted with ethyl acetate. The organic layer is washed with saturated sodium chloride, dried over magnesium sulfate, and concentrated. The residue is chromatographed over silica gel, eluting with a gradient of hexanes to 10% ethyl acetate in hexanes. Concentration provides ethyl 3-cycloheptyl-3-oxo-2-(2,4,6-trifluorophenyl)propanoate as a colorless oil (410 mg). MS: m/z 341.2 (M−H).

Step B: 7-Chloro-5-cycloheptyl-6-(2,4,6-trifluorophenyl)imidazo[1,2-a]pyrimidine A mixture of ethyl 3-cycloheptyl-3-oxo-2-(2,4,6-trifluorophenyl)propanoate (342 mg, 1.0 mmol), 2-aminoimidazole (Helv. Acta. Chim. 76, 2066 (1993)) (83 mg, 1.0 mmol), and 0.5 mL of tributylamine is stirred under nitrogen atmosphere at 160° C. for 1.5 h and cooled to room temperature. The mixture is dissolved in ethyl acetate and the organic layer is washed with 1.0 N hydrochloric acide (×2) and saturated sodium chloride, dried over magnesium sulfate, and concentrated to give crude 5-cycloheptyl-6-(2,4,6-trifluorophenyl)imidazo[1,2-a]pyrimidin-7-ol as a dark oil (294 mg).

A mixture of the above 5-cycloheptyl-6-(2,4,6-trifluorophenyl)imidazo[1,2-a]pyrimidin-7-ol (294 mg) in 2 mL of phosphorous oxychloride is heated at reflux for 6 h. The excess phosphorous oxychloride is removed in vaccuo, and the resulting residue is dissolved in methylene chloride. The organic layer is washed with water, dried over magnesium sulfate, and concentrated. The residue is chromatographed over silica gel, eluting with a gradient of 10% ethyl acetate in hexanes to 33% ethyl acetate in hexanes. Concentration provides 7-chloro-5-cycloheptyl-6-(2,4,6-trifluorophenyl)imidazo[1,2-a]pyrimidine as a white solid (24 mg). MS: m/z 380.2 (M+H).

EXAMPLE 6

3-[4-(7-Chloro-5-cycloheptylimidazo[1,2-a]pyrimidin-6-yl)-3,5-difluorophenoxy]-N,N-dimethylpropan-1-amine;

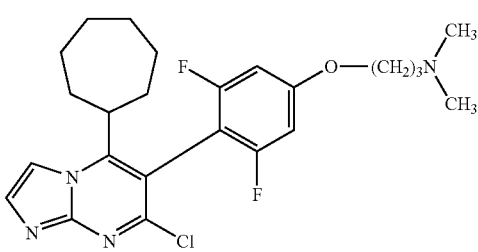

A mixture of ethyl 3-cycloheptyl-3-oxo-2-(2,4,6-trifluorophenyl)propanoate (342 mg, 1.0 mmol), 2-aminoimidazole (Hel. Acta. Chim. 76, 2066 (1993)) (83 mg, 1.0 mmol), and 0.5 mL of tributylamine is stirred under nitrogen atmosphere at 160° C. for 1.5 h and cooled to room temperature.

The mixture is dissolved in ethyl acetate and the organic layer is washed with 1.0 N hydrochloric acide (×2) and saturated sodium chloride, dried over magnesium sulfate, and concentrated to give crude 5-cycloheptyl-6-(2,4,6-trifluorophenyl)imidazo[1,2-a]pyrimidin-7-ol as a dark oil.

To a solution of the above 5-cycloheptyl-6-(2,4,6-trifluorophenyl)imidazo[1,2-a]pyrimidin-7-ol and 3-dimethylamino-1-propanol (206 m g, 2.0 mmol) in 3.0 mL of dimethylsulfoxide at room temperature is added sodium hydride (60% in mineral oil, 80 mg, 2.0 mmol). The mixture is heated at 40° C. for 2 h, and cooled to room temperature. A saturated sodium chloride solution is added, and the product is extracted with ehtyl acetate. The organic solution is washed with saturated sodium chloride (×3), dried over magnesium sulfate, and concentrated. To the residue is added 5 mL of phosphorous oxychloride and 2 mL of N,N-diethylaniline, and the mixture is heated at 110° C. for 1 h. The excess phosphorous oxychloride is removed in vaccuo, and the resulting residue is partitioned between ethyl acetate and 5% sodium carbonate solution. The organic layer is washed with saturated sodium chloride, dried over magnesium sulfate, and concentrated. The residue is chromatographed over silica gel, eluting with a gradient of ethyl acetate to 20% methyl alcohol in ethyl acetate. Concentration provides 3-[4-(7-chloro-5-cycloheptylimidazo[1,2-a]pyrimidin-6-yl)-3,5-difluorophenoxy]-N,N-dimethylpropan-1-amine as a brown oil (24 mg). MS: m/z 463.3 (M+H).

Diethyl 2-(2,4,6-trifluorophenyl)malonate is disclosed in U.S. Pat. No. 6,156,925. 2-Aminoimidazole is prepared as described in *Helv. Acta. Chim.* 76, 2066 (1993).

What is claimed is:

1. A compound represented by Formula (I):

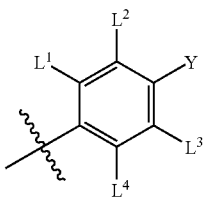
(I)

wherein:

$R^1$ is selected from

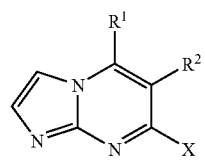 and $C_6-C_8$ cycloalkyl;

$R^2$ is a moiety of the formula

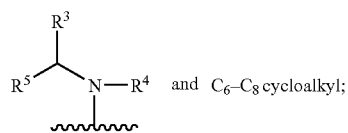

$R^3$ is H, or $C_1-C_3$ alkyl;
$R^4$ is H, or $C_1-C_3$ alkyl; or
$R^3$ and $R^4$ when optionally taken together form a 6 to 8 membered saturated heterocyclic ring having 1-2 nitrogen atoms, 0-1 oxygen atoms and 0-1 sulfur atoms, and optionally substituted with $C_1-C_3$ alkyl;
$R^5$ is H, $C_1-C_3$ alkyl or $C_1-C_3$ fluoroalkyl;
Y is a moiety of the formula $-O(CH_2)_nQ$;
n is an integer of 2, 3 or 4;
Q is $-OH$, or $-NR^6R^7$;
$R^6$ and $R^7$ are independently H or $C_1-C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1-C_3$alkyl;
$L^1, L^2, L^3$, and $L^4$ are each independently H, F, Cl, Br or $CF_3$;
X is Cl or Br;

or pharmaceutically acceptable salts thereof.

2. A compound according to claim 1 wherein $R^2$ is a moiety of the formula

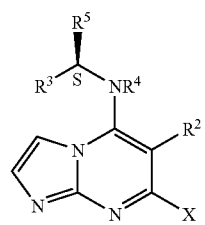

or pharmaceutically acceptable salts thereof.

3. A compound according to claim 1 wherein Formula (I) is represented by Formula (Ia):

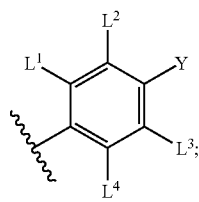
(Ia)

4. A compound according to claim 3 wherein:
$R^2$ is

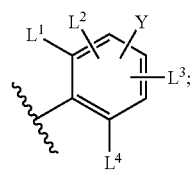

n is 3;
X is Cl or Br;
Y is a moiety of the formula $-O-(CH_2)_nQ$;
$R^3$ is H or methyl;
$R^4$ is H;
Q is $-NR^6R^7$;
$R^5$ is $CF_3$;
$R^6$ and $R^7$ are each independently H or $C_1-C_3$ alkyl; or
$R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are F;
$L^2$ and $L^3$ are H;
or pharmaceutically acceptable salts thereof.

5. A compound according to claim 3 wherein:
$R^2$ is

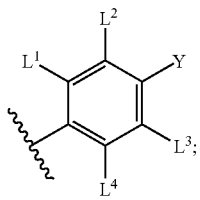

X is Cl;
n is 3;
Y is —O(CH$_2$)$_n$Q;
Q is —NR$^6$R$^7$;
$R^3$ is H or methyl;
$R^4$ is H;
$R^5$ is CF$_3$;
$R^6$ is methyl;
$R^7$ is H or methyl;
$L^1$ and $L^4$ are F;
$L^2$ and $L^3$ are H;
or pharmaceutically acceptable salts thereof.

6. A compound according to claim 1 wherein Formula (I) is represented by Formula (Ib):

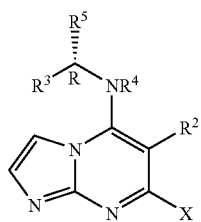

(Ib)

or pharmaceutically acceptable salts thereof.

7. A compound according to claim 6 wherein:
$R^2$ is

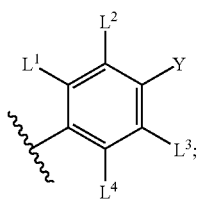

n is 3;
X is Cl or Br;
Y is a moiety of the formula —O—(CH$_2$)$_n$Q;
$R^3$ is H or methyl;
$R^4$ is H;
Q is —NR$^6$R$^7$;
$R^5$ is CF$_3$;
$R^6$ and $R^7$ are each independently H or $C_1$-$C_3$ alkyl; or $R^6$ and $R^7$ when optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$ and $L^4$ are F;
$L^2$ and $L^3$ are H;
or pharmaceutically acceptable salts thereof.

8. A compound according to claim 6 wherein:
$R^2$ is

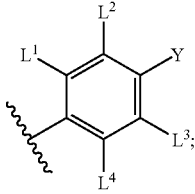

n is 3;
X is Cl;
Y is a moiety of the formula —O(CH$_2$)$_n$Q;
Q is —NR$^6$R$^7$;
$R^4$ is H;
$R^6$ is methyl;
$R^7$ is H or methyl;
$L^1$ and $L^4$ are F;
$L^2$ and $L^3$ are H;
or pharmaceutically acceptable salts thereof.

9. The compound according to claim 1 wherein $R^1$ is $C_6$-$C_8$ cycloalkyl or pharmaceutically acceptable salts thereof.

10. A compound according to claim 1 wherein:
$R^1$ is $C_6$-$C_8$ cycloalkyl;
$R^2$ is

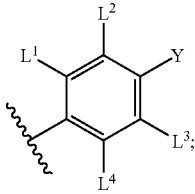

n is 3;
X is Cl;
Y is a moiety of the formula —O(CH$_2$)$_n$Q;
Q is —NR$^6$R$^7$;
$R^6$ is methyl;
$R^7$ is H or methyl;
$L^1$ and $L^4$ are F;
$L^2$ and $L^3$ are H;
or pharmaceutically acceptable salts thereof.

11. A compound according to claim 1 selected from the group:
7-Chloro-6-{4-[3-(dimethylamino)propoxy]-2,6-difluorophenyl}-N-(2,2,2-trifluoroethyl)imidazo[1,2-a]pyrimidin-5-amine,
3-[4-(7-Chloro-5-cycloheptylimidazo[1,2-a]pyrimidin-6-yl)-3,5-difluorophenoxy]-N,N-dimethylpropan-1-amine,
7-Chloro-6-{4-[4-(dimethylamino)butoxy]-2,6-difluorophenyl}-N-(2,2,2-trifluoroethyl)imidazo[1,2-a]pyrimidin-5-amine, N-{3-[4-(7-chloro-5-cyclohexylimidazo[1,2-a]pyrimidin-6-yl)-3,5-difluorophenoxy]propyl}-N,N-dimethylamine, 7-chloro-6-{2,6-difluoro-4-[3-(methylamino)propoxy]phenyl}-N-(-2,2,2-trifluoro-1-methylethyl)imidazo[1,2-a]pyrimidin-5-amine and 7-chloro-6-{4-[3-(dimethylamino)propoxy]-2,6-difluorophenyl}-N-(-2,2,2-trifluoro-1-methylethyl)imidazo[1,2-a]pyrimidin-5-amine.

12. A compound according to claim 4, selected from the group 7-chloro-6-{2,6-difluoro-4-[3-(methylamino)propoxy]phenyl}-N-[(1S)-2,2,2-trifluoro-1-methylethyl]imidazo[1,2-a]pyrimidin-5-amine and 7-chloro-6-{4-[3-(dimethylamino)propoxy]-2,6-difluorophenyl}-N-[(1S)-2,2,2-trifluoro-1-methylethyl]imidazo[1,2-a]pyrimidin-5-amine or pharmaceutically acceptable salts thereof.

13. A compound according to claim 7, selected from the group 7-chloro-6-{2,6-difluoro-4-[3-(methylamino)propoxy]phenyl}-N-[(1R)-2,2,2-trifluoro-1-methylethyl]imidazo[1,2-a]pyrimidin-5-amine and 7-chloro-6-{4-[3-(dimethylamino)propoxy]-2,6-difluorophenyl}-N-[(1R)-2,2,2-trifluoro-1-methylethyl]imidazo[1,2-a]pyrimidin-5-amine or a pharmaceutically acceptable salts thereof.

14. A pharmaceutical composition which comprises an effective amount of a compound of claim 1 or a pharmaceutically acceptable salt thereof together with a pharmaceutically acceptable carrier.

15. A process for the preparation of a compound of Formula (I)

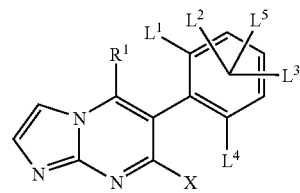

wherein:
R$^1$ is selected from

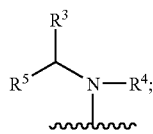

R$^2$ is a moiety of the formula

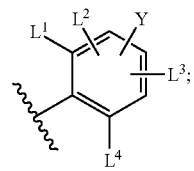

R$^3$ is H, or C$_1$-C$_3$ alkyl;
R$^4$ is H, or C$_1$-C$_3$ alkyl; or
R$^3$ and R$^4$ optionally taken together form a 6 to 8 membered saturated heterocyclic ring having 1-2 nitrogen atoms, 0-1 oxygen atoms and 0-1 sulfur atoms, and optionally substituted with C$_1$-C$_3$ alkyl;
R$^5$ is H, C$_1$-C$_3$ alkyl or C$_1$-C$_3$ fluoroalkyl;
Y is a moiety of the formula —O(CH$_2$)$_n$Q;
n is an integer of 2, 3 or 4;
Q is —OH, or —NR$^6$R$^7$;
R$^6$ and R$^7$ are independently H or C$_1$-C$_3$ alkyl; or R$^6$ and R$^7$ optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with R$^8$;
R$^8$ is C$_1$-C$_3$ alkyl;
L$^1$, L$^2$, L$^3$, and L$^4$ are each independently H, F, Cl, Br or CF$_3$;
X is Cl or Br;
or pharmaceutically acceptable salts thereof
comprising the step of reacting a compound of the formula

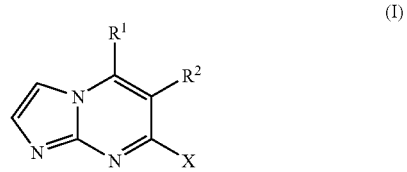

where L$^5$ is a leaving group with a compound of the formula HO—(CH$_2$)$_n$Q in the presence of a strong base optionally in the presence of an aprotic solvent to give a compound of Formula (I).

16. A process according to claim 15 wherein the leaving group is F and Q is NR$^6$R$^7$.

17. A process according to claim 15 wherein the strong base is selected from an alkali metal hydroxide, alkali metal carbonate and alkali hydride.

18. A process according to claim 15 wherein the aprotic solvent is selected from dimethylsulfoxide and dimethylformamide.

19. A process for the preparation of a compound of Formula (I)

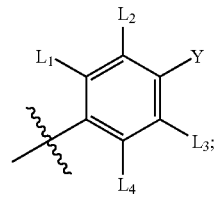

wherein:
R$^1$ is C$_6$-C$_8$ cycloalkyl;
R$^2$ is a moiety

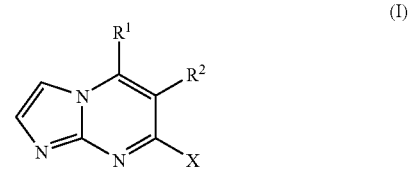

Y is a moiety of the formula —O(CH$_2$)$_n$Q;
n is an integer of 2, 3 or 4;
Q is —NR$^6$R$^7$;
R$^6$ and R$^7$ are independently H or C$_1$-C$_3$ alkyl; or
R$^6$ and R$^7$ optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with R$^8$;
R$^8$ is C$_1$-C$_3$ alkyl;
L$^1$, L$^2$, L$^3$, and L$^4$ are each independently H, F, Cl, Br or CF$_3$;
X is Cl or Br;
or pharmaceutically acceptable salts thereof comprising the steps of:

a) reacting an ester of the formula,

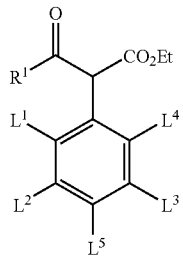

where $L^5$ is a leaving group, with 2-aminoimidazole in the presence of a tertiary amine in an aprotic solvent to provide compound (V) of the formula

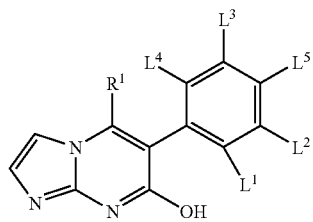

(V)

b) reacting compound (V) with an alcohol of the formula $HO(CH_2)_nQ$ in the presence of a strong base in a solvent to afford compound (VI)

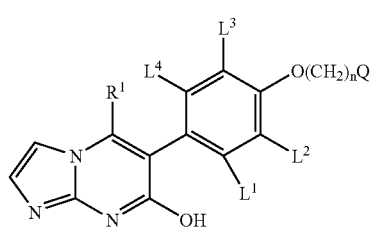

(VI)

c) halogenating compound (VI) with $POX_3$ to afford a compound of Formula (I).

20. A process according to claim 19 wherein the base is selected from an alkali metal hydroxide, alkali metal carbonate and alkali hydride.

21. A process according to claim 19 wherein the solvent is selected from dimethylsulfoxide and dimethylformamide.

22. A compound of Formula (I)

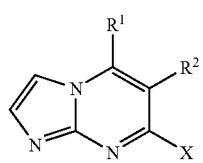

(I)

wherein:

$R^1$ is selected from

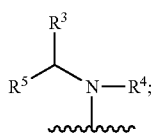

$R^2$ is a moiety of the formula

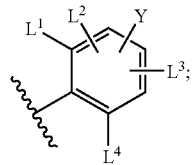

$R^3$ is H, or $C_1$-$C_3$ alkyl;
$R^4$ is H, or $C_1$-$C_3$ alkyl; or
$R^3$ and $R^4$ optionally taken together form a 6 to 8 membered saturated heterocyclic ring having 1-2 nitrogen atoms, 0-1 oxygen atoms and 0-1 sulfur atoms, and optionally substituted with $C_1$-$C_3$ alkyl;
$R^5$ is H, $C_1$-$C_3$ alkyl or $C_1$-$C_3$ fluoroalkyl;
Y is a moiety of the formula —$O(CH_2)_nQ$;
n is an integer of 2, 3 or 4;
Q is —OH, or —$NR^6R^7$;
$R^6$ and $R^7$ are independently H or $C_1$-$C_3$ alkyl; or
$R^6$ and $R^7$ optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$, $L^2$, $L^3$, and $L^4$ are each independently H, F, Cl, Br or $CF_3$;
X is Cl or Br;

or pharmaceutically acceptable salts thereof
produced by the process which comprises reacting a compound of the formula

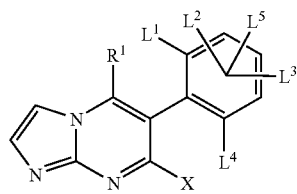

where $L^5$ is a leaving group with a compound of the formula HO—$(CH_2)_nQ$ in the presence of a strong base optionally in the presence of an aprotic solvent to give a compound of Formula (I).

23. A compound produced by the process according to claim 22 wherein the leaving group is F and Q is $NR^6R^7$.

24. A compound produced by process according to claim 22 wherein the strong base is selected from an alkali metal hydroxide, alkali metal carbonate and alkali hydride.

25. A compound produced by the process according to claim 22 wherein the aprotic solvent is selected from dimethylsulfoxide and dimethylformamide.

26. A compound of Formula (I)

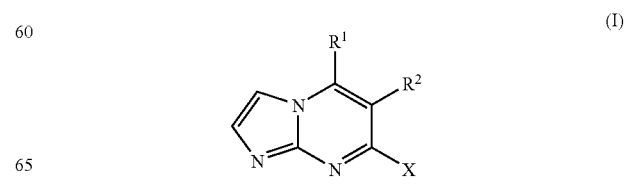

(I)

wherein:
$R^1$ is $C_6$-$C_8$ cycloalkyl;
$R^2$ is a moiety

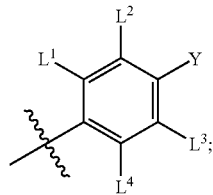

Y is a moiety of the formula —O(CH$_2$)$_n$Q;
n is an integer of 2, 3 or 4;
Q is —NR$^6$R$^7$;
$R^6$ and $R^7$ are independently H or $C_1$-$C_3$ alkyl; or
$R^6$ and $R^7$ optionally taken together with the nitrogen atom to which each is attached form a 4 to 6 membered saturated heterocyclic ring having 1-2 nitrogen atoms, 0-1 oxygen atoms and 0-1 sulfur atoms, and optionally substituted with $R^8$;
$R^8$ is $C_1$-$C_3$ alkyl;
$L^1$, $L^2$, $L^3$, and $L^4$ are each independently H, F, Cl, Br or CF$_3$;
X is Cl or Br;
or pharmaceutically acceptable salts thereof
produced by the process which comprises
a) reacting an ester of the formula,

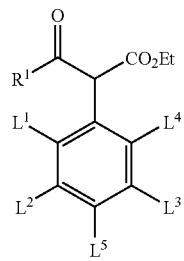

where $L^5$ is a leaving group, with 2-aminoimidazole in the presence of a tertiary amine in an aprotic solvent to provide compound (V) of the formula

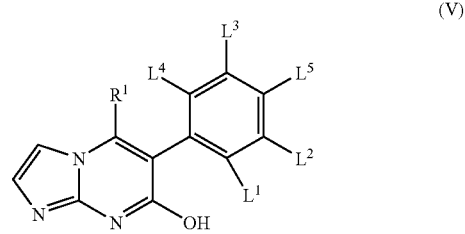

(V)

b) reacting compound (V) with an alcohol of the formula HO(CH$_2$)$_n$Q in the presence of a strong base in a solvent to afford compound (VI)

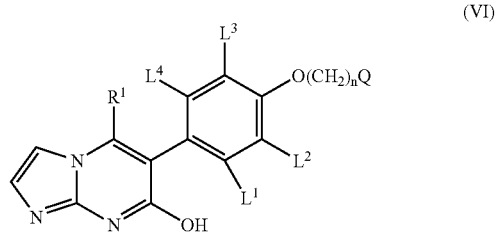

(VI)

c) halogenating compound (VI) with POX$_3$ to afford a compound of Formula (I).

27. A compound produced by the process according to claim 26 wherein the strong base is selected from an alkali metal hydroxide, alkali metal carbonate and alkali hydride.

28. A compound produced by the process according to claim 26 wherein the solvent is selected from dimethylsulfoxide and dimethylformamide.

* * * * *